(12) United States Patent
Segall et al.

(10) Patent No.: US 9,367,812 B2
(45) Date of Patent: Jun. 14, 2016

(54) COMPOUND SELECTION IN DRUG DISCOVERY

(75) Inventors: Matthew Segall, Ely (GB); Tatsunori Hashimoto, Woodside, CA (US)

(73) Assignee: Optibrium Ltd., Cambridge (GB)

( * ) Notice: Subject to any disclaimer, the term of this patent is extended or adjusted under 35 U.S.C. 154(b) by 437 days.

(21) Appl. No.: 13/261,542

(22) PCT Filed: Aug. 25, 2010

(86) PCT No.: PCT/US2010/046614
§ 371 (c)(1),
(2), (4) Date: Dec. 19, 2012

(87) PCT Pub. No.: WO2012/026929
PCT Pub. Date: Mar. 1, 2012

(65) Prior Publication Data
US 2013/0173503 A1 Jul. 4, 2013

(51) Int. Cl.
G06N 99/00 (2010.01)
G06F 19/00 (2011.01)

(52) U.S. Cl.
CPC ............ G06N 99/005 (2013.01); G06F 19/704 (2013.01)

(58) Field of Classification Search
None
See application file for complete search history.

(56) References Cited

U.S. PATENT DOCUMENTS

| | | | | |
|---|---|---|---|---|
| 6,829,540 B1 * | 12/2004 | Pidgeon | ................ | G06F 19/704 422/50 |
| 2001/0041964 A1 * | 11/2001 | Grass | ...................... | C40B 50/02 702/19 |
| 2004/0009536 A1 * | 1/2004 | Grass | ..................... | G06F 19/704 435/7.2 |
| 2004/0117125 A1 * | 6/2004 | Chen | ...................... | G06F 19/707 702/19 |
| 2004/0180322 A1 * | 9/2004 | Grass | .................. | G06F 19/3437 435/4 |
| 2008/0033899 A1 * | 2/2008 | Barnhill | .................. | G06F 19/24 706/48 |
| 2009/0291898 A1 * | 11/2009 | Hicks | ...................... | G06F 19/16 514/1.1 |
| 2010/0063948 A1 * | 3/2010 | Virkar | ...................... | G06N 3/02 706/12 |
| 2013/0173503 A1 * | 7/2013 | Segall | .................. | G06N 99/005 706/12 |

FOREIGN PATENT DOCUMENTS

| | | | | |
|---|---|---|---|---|
| WO | WO 2012/026929 A1 * | 3/2012 | ............... | C12Q 1/00 |
| WO | WO 2012026929 A1 * | 3/2012 | ............ | G06F 19/704 |

OTHER PUBLICATIONS

International Preliminary Report on Patentability, IPEA/US, Aug. 31, 2012.
International Search Report and the Written Opinion of the International Searching Authority, ISA/US, Oct. 14, 2010.
Warmuth et al., Active Learning With Support Vector Machines in the Drug Discovery Process, Journal of Chemical Information and Computer Sciences 2003, vol. 43, No. 2 (Feb. 12, 2003).

* cited by examiner

*Primary Examiner* — Kakali Chaki
*Assistant Examiner* — Fuming Wu
(74) *Attorney, Agent, or Firm* — Wright IP & International Law; Eric G. Wright

(57) ABSTRACT

Methods and systems for determining the selection criteria that in its embodiments can distinguish compounds that successfully meet an objective from those that do not, determine the importance of selection criterion in selecting test compounds that have a high probability of achieving an objective and automatically apply the selection criteria to select test compounds with a high chance of meeting an objective.

19 Claims, 16 Drawing Sheets

Probability Densities for Orally Bioavailable Scores for Oral and Non-oral Compounds

COMPOUND SELECTION IN DRUG DISCOVERY

FIELD OF THE INVENTION

Methods and systems for analysis of compounds.

BACKGROUND OF THE INVENTION

Drug discovery project teams are faced with many difficult and problematic decisions which range, e.g., from choosing the best target for a potential therapeutic indication to selection of appropriate compounds in hit finding, hit-to-lead, lead optimization and nomination of a preclinical candidate. Poor decisions can result in failed drug discovery projects. A poor choice of a target or a compound can result in financial loss and wasted efforts due to unnecessary synthesis and screening, or late stage failure of research projects. Conversely, over-aggressive filtering of the drug pipelines can lead to missed opportunities to find new therapies. Experimental techniques, predictive modeling and informatics, have not solved the enormous challenges facing drug discovery research. The average cost per new molecular entity (NME) launched on the market has risen from an estimated $805 million in 2003 (Dimasi, J A, R W Hansen, and H G Grabowski, "The price of innovation: new estimates of drug development costs." *J. health Econ.* 22 (2003): 151-85.) to $1.7 billion (Paul, S M, et al. "How to improve R&D productivity: the pharmaceutical industry's grand challenge." *Nat. Rev. Drug Discov.* 9 (2010): 203-14), while the success rate of compounds entering preclinical development remains poor and unchanged at a mere approximately 8% (Id.).

Making good decisions in drug discovery is an enormous challenge and the known approaches often fail to meet drug discovery objectives. Historically, throughout the drug discovery process, compounds are selected for progression for further study on the basis of the data that have been generated up to that point. The criteria by which compounds are selected are generally based on the opinions of experts in the field. In some research, 'Lipinski's Rule of Five,' (Lipinski, C. A., F. Lombardo, B. W. Dominy, and P. J. Feeney. "Experimental and computational approaches to estimate solubility and permeability in drug discovery and development settings." *Adv. Drug Deliv. Rev.* 23 (1997): 3-25) has been applied which are criteria for four basic characteristics of compounds, namely: Number of hydrogen bond donors<5; Number of hydrogen bond acceptors<10; Molecular weight<500; and log P<5.

This 'manual' approach to determining the selection criteria for compounds is unsatisfactory and has a number of problems and disadvantages. Criteria set on the basis of expert's opinions are colored by individual biases and are limited to the experience of those experts, so cannot take into consideration large amounts of historical data. This makes it difficult to apply criteria based on broad experience gained across many drug discovery projects. Further, the increasing complexity of the data available in drug discovery makes a 'manual' approach to analysis of the data to elucidate selection criteria intractable. For example, this problem is readily apparent in fields such as toxicology, where many early in vitro assays have been developed in an attempt to identify safe compounds and eliminate from consideration compounds that can be toxic to animals or humans. Given the wealth of potential assays that can be applied, it is difficult or not currently possible to identify those that are most important (or even critical) to identifying safe compounds and what selection criteria should be applied to the results from such assays.

Certain computational approaches to predicting outcomes for compounds have been employed in drug discovery. Quantitative Structure Activity Relationship (QSAR) models have been applied to predicting individual properties of compounds, such as solubility, lipophilicity, absorption, metabolism and activity against drug targets. QSAR models have also been developed for predicting certain, in vivo, outcomes. But, these are insufficient to solve the problems outlined above.

Different methods have been used to generate QSAR models, e.g., Partial Least Squares (PLS), Classification and Regression Trees (CART), Random Forest (RF), Support Vector Machines (SVM), Artificial Neural Networks (ANN) and Gaussian Processes (GP). None have solved the challenges that drug researchers face, e.g.: PLS generates linear models which have a low accuracy where there are complex relationships between the descriptors and the outcome being modelled; CART generates models which lack predictive power for complex outcomes and it is difficult to determine the importance of each descriptor in determining the outcome; and non-linear techniques such as SVM, ANN and GP have been tried but fail because the relationships between descriptors used by the techniques and outcomes can not be usefully or reasonably determined.

SUMMARY OF THE INVENTION

A first embodiment of the invention is a method executed on a computer for analysis of compound data. This embodiment utilizes the method step of providing a computer having a memory. Herein, "method step" and "step" are used synonymously in the context of the steps of the embodiments of the method. This first embodiment of the method in a step provides to the memory a training data from a training data set comprising at least one training compound with at least one property value for each training compound. This embodiment of the method in a step provides to the memory a data identifying each training compound as achieving an objective or not achieving the objective. This embodiment of the method employs a step in which the computer can run program executable code on the training data set. This embodiment includes a method step in which the program executable code can determine at least one selection criteria for each of at least one of the properties in the training data set, each of the selection criteria corresponding to a property value or range of property values, such that those training compounds in the training data set which meet the selection criteria have a higher probability of meeting the objective than the average of the training compounds in the training data set. The first embodiment optionally utilizes a step of providing a data of the objective to the memory. The objective optionally can be a drug discovery objective. This embodiment includes a method step in which the program executable code can determine an importance value for each selection criterion. The method of the first embodiment can further use program executable code in a step calculating the importance value of each selection criterion by determining a ratio between a probability that a training compound meeting a selection criterion achieves the objective and the probability that a training compound that does not meet the selection criterion achieves the objective. The method of the first embodiment can optionally utilize a step in which the objective is a drug discovery objective. The method of the first embodiment can also use program executable code in a step calculating the importance value of each selection criterion and to determine a ratio between the probability that a training compound meeting a selection criterion achieves a drug discovery objective and a probability that a training compound that does not meet the selection criterion achieves the drug discovery objective.

A second embodiment of the invention is a method executed on a computer for analysis of compound data. This embodiment utilizes the step of providing a computer having a memory. The second embodiment optionally utilizes a step of providing a data of an objective to the memory. This embodiment of the method in a step provides to the memory a training data from a training data set comprising at least one training compound with at least one property value for each training compound. This embodiment of the method in a step provides to the memory a data identifying each training compound as achieving an objective or not achieving the objective. This embodiment of the method employs a step in which the computer can run a program executable code on the training data set defining a box in the space of properties containing all of the training compounds in the training data set. This embodiment of the method employs a step in which the computer can run a program executable code performing one or more peeling steps, removing a proportion of the training compounds $\gamma$, with $\gamma$ can take a value greater than 0 and less than 1. This embodiment of the method employs a step in which the computer can run a program executable code performing zero or more pasting steps, adding back a proportion of the training compounds $\beta$, with $\beta$ can take a value greater than 0 and less than 1. This embodiment of the method employs a step in which the computer can run a program executable code determining the selection criteria corresponding to the boundaries of the resulting box. This embodiment of the method employs a step in which the computer can run a program executable code removing the training compounds in the box from the training data set. This embodiment of the method employs a step in which the computer can run a program executable code repeating processing steps (e.g., iterating calculations, program executable code or logic) until a stopping condition has been met. The method of the second embodiment can use a drug discovery objective.

A third embodiment of the invention is a method executed on a computer for analysis of compound data. This embodiment utilizes the step of providing a computer having a memory. This embodiment of the method in a step provides to the memory a training data from a training data set comprising at least one training compound with at least one property value for each training compound. This embodiment of the method in a step provides to the memory a data identifying each training compound as achieving an objective or not achieving the objective. This embodiment of the method employs a step in which the computer can run a program executable code on the training data set defining a box in the space of properties containing all of the training compounds in the training data set. This embodiment of the method employs a step in which the computer can run a program executable code performing one or more peeling steps, removing a proportion of the training compounds $\gamma$, with $\gamma$ can take a value greater than 0 and less than 1. This embodiment of the method employs a step in which the computer can run a program executable code performing zero or more pasting steps, adding back a proportion of the training compounds $\beta$, with $\beta$ can take a value greater than 0 and less than 1. This embodiment of the method employs a step in which the computer can run a program executable code determining the selection criteria corresponding to the boundaries of the resulting box. This embodiment of the method employs a step in which the computer can run a program executable code removing the training compounds in the box from the training data set. This embodiment of the method employs a step in which the computer can run a program executable code repeating processing steps (e.g., iterating calculations, program executable code or logic) until a stopping condition has been met. This embodiment of the method employs a step in which the computer can run a program executable code determining an importance value for each selection criterion. The method of the third embodiment can continue with the step of determining an importance value for each selection criteria can use the step of the computer can run a program executable code calculating the importance value for each selection criterion by determining the ratio between the probability that a training compound meeting a selection criterion achieves the objective and the probability that a training compound that does not meet the selection criterion achieves the objective. The method of the third embodiment can optionally utilize a step in which the objective is a drug discovery objective. The method of the third embodiment can also continue with a step of determining an importance value for each selection criteria can use the step of the computer can run a program executable code calculating the importance value for each selection criterion by determining the ratio between the probability that a training compound meeting a selection criterion achieves a drug discovery objective and the probability that a training compound that does not meet the selection criterion achieves the drug discovery objective.

A fourth embodiment of the invention is a method executed on a computer for analysis of compound data. This embodiment utilizes the step of providing a computer having a memory. This embodiment of the method optionally provides a data of an objective to the memory. This embodiment of the method in a step provides to the memory a training data from a training data set comprising at least one training compound with at least one property value for each training compound. This embodiment of the method in a step provides to the memory a data identifying each training compound as achieving the objective or not achieving the objective. This embodiment of the method employs a step in which the computer can run a program executable code on the training data set determining at least one selection criteria for each of at least one of the properties in the training data set, each of the selection criteria corresponding to a property value or range of property values, such that those training compounds in the training data set that meet the selection criteria have a higher probability of meeting the drug discovery objective than the average of the training compounds in the training data set. This embodiment of the method employs a step in which the computer can run a program executable code determining an importance value for each selection criterion. This embodiment of the method provides a test data set comprising at least one test compound and at least one property value for each test compound, with at least one test compound having a property which can be compared to a property of a training compound having a value present in the training data set. This embodiment of the method employs a step in which the computer can run a program executable code applying one or more of the selection criteria to identify test compounds that meet the selection criteria. The method of the fourth embodiment can optionally utilize a step in which the objective is a drug discovery objective. The method of the fourth embodiment can continue with the step of determining an importance value for each selection criterion, further uses the steps of the computer outputting the selection criteria and corresponding importance values reflecting the importance of each criterion, and receiving into the memory a user input to modify the selection criteria and/or importance value of one or more selection criterion. The method of the fourth embodiment can further use the steps of the computer outputting at least one value for each test compound in the test set, indicating those test compounds most likely to meet the drug discovery objective. The method of the fourth embodiment can use the step of determining an importance value for each selection criteria and can use the step of the computer can run a program executable code calculating the importance value for each selection criterion by determining the ratio between the probability that a training compound meeting a selection criterion achieves an objective and the probability that a training compound that does not meet the selection criterion achieves the objective. The method of the fourth embodiment can continue with the step of determining an importance value for each selection criterion, further uses the steps of the computer outputting the selection criteria and corresponding importance values reflecting the importance of each criterion, and receiving into the memory a user input to modify the selection criteria and/or importance value of one or more selection criterion. The method of the fourth embodiment further uses the steps of the computer outputting at least one value for each test compound in the test set, and the computer can run a program executable code indicating those test compounds most likely to meet the drug discovery objective. The method of the fourth embodiment can continue with the step of determining an importance value for each selection criteria can use the step of the computer can run a program executable code calculating the importance value for each selection criterion by determining the ratio between the probability that a training compound meeting a selection criterion achieves the drug discovery objective and the probability that a training compound that does not meet the selection criterion achieves the drug discovery objective.

A fifth embodiment of the invention is a method executed on a computer for analysis of compound data. This embodiment utilizes the step of providing a computer having a memory. This embodiment of the method in a step provides to the memory a training data from a training data set comprising at least one training compound with at least one property value for each training compound. This embodiment of the method in a step provides to the memory a data identifying each training compound as achieving an objective or not achieving the objective. This embodiment of the method employs a step in which the computer can run a program executable code on the training data set defining a box in the space of properties containing all of the training compounds in the training data set. This embodiment of the method employs a step in which the computer can run a program executable code performing one or more peeling steps, removing a proportion of the training compounds γ, with γ can take a value greater than 0 and less than 1. This embodiment of the method employs a step in which the computer can run a program executable code performing zero or more pasting steps, adding back a proportion of the training compounds β, with here β can take a value greater than 0 and less than 1. This embodiment of the method employs a step in which the computer can run a program executable code determining the selection criteria corresponding to the boundaries of the resulting box. This embodiment of the method employs a step in which the computer can run a program executable code removing the training compounds in the box from the training data set. This embodiment of the method employs a step in which the computer can run a program executable code repeating processing steps (e.g., iterating calculations, program executable code or logic) until a stopping condition has been met. This embodiment of the method in a step provides to the memory a test data set comprising at least one test compound and at least one property value for each test compound, with at least one test compound having a property which can be compared to a property of a training compound having a value present in the training data set. This embodiment of the method employs a step in which the computer can run a program executable code applying one or more of the selection criteria to identify test compounds that meet the selection criteria. The method of the fifth embodiment can optionally utilize a step in which the objective is a drug discovery objective. The method of the fifth embodiment can continue with the step of repeating processing steps (e.g., iterating calculations, program executable code or logic) until a stopping condition has been met further uses the steps of the computer outputting the selection criteria, and receiving into the memory a user input to modify the selection criteria. The method of the fifth embodiment further using the steps of outputting at least one value for each test compound in the test set, indicating those test compounds most likely to meet the objective. The method of the fifth embodiment can continue with the step of repeating processing steps (e.g., iterating calculations, program executable code or logic) until a stopping condition has been met further uses the steps of the computer outputting the selection criteria, and receiving into the memory a user input to modify the selection criteria. The method of the fifth embodiment further uses the steps of the computer outputting at least one value for each test compound in the test set, indicating those test compounds most likely to meet the drug discovery objective.

A sixth embodiment of the invention is a method executed on a computer for selection of compounds. This embodiment utilizes the step of providing a computer having a memory. This embodiment of the method in a step provides to the memory a training data from a training data set comprising at least one training compound with at least one property value for each training compound. This embodiment of the method in a step provides to the memory a data identifying each training compound as achieving an objective or not achieving the objective. This embodiment of the method employs a step in which the computer can run a program executable code on the training data set defining a box in the space of properties containing all of the training compounds in the training data set. This embodiment of the method employs a step in which the computer can run a program executable code performing one or more peeling steps, removing a proportion of the training compounds γ, with γ can take a value greater than 0 and less than 1. This embodiment of the method employs a step in which the computer can run a program executable code performing zero or more pasting steps, adding back a proportion of the training compounds β, with β can take a value greater than 0 and less than 1. This embodiment of the method employs a step in which the computer can run a program executable code determining the selection criteria corresponding to the boundaries of the resulting box. This embodiment of the method employs a step in which the computer can run a program executable code removing the training compounds in the box from the training data set. This embodiment of the method employs a step in which the computer can run a program executable code repeating processing steps (e.g., iterating calculations, program executable code or logic) until a stopping condition has been met. This embodiment of the method employs a step in which the computer can run a program executable code determining an importance value for each selection criterion. This embodiment of the method provides a test data from a test data set comprising at least one test compound and at least one property value for each test compound, with at least one test compound having a property which can be compared to a property of a training compound having a value present in the training data set. This embodiment of the method employs a step in which the computer can run a program executable code applying one or more of the selection criteria to identify test compounds that meet the selection criteria. The method of the sixth embodiment can optionally utilize a step in which the objective is a drug discovery objective. The method of the sixth embodiment can continue with the step of determining an importance value for each selection criterion further uses the steps of the computer outputting the selection criteria and corresponding importance values reflecting the importance of each criterion, and receiving into the memory a user input to modify the selection criteria and/or importance value of one or more selection criterion. The method of the sixth embodiment can further use the steps of the computer outputting at least one value for each test compound in the test set, indicating those test compounds most likely to meet the objective. The method of the sixth embodiment can continue with the step of determining an importance value for each selection criteria can use the step of the computer can run a program executable code calculating the importance value for each selection criterion by determining the ratio between the probability that a training compound meeting a selection criterion achieves an objective and the probability that a training compound that does not meet the selection criterion achieves the objective. The method of the sixth embodiment further uses the steps of the computer outputting at least one value for each test compound in the test set, indicating those test compounds most likely to meet the drug discovery objective. The method of the sixth embodiment can also use a step of determining an importance value for each selection criteria can use the step of the computer can run a program executable code calculating the importance value for each selection criterion by determining the ratio between the probability that a training compound meeting a selection criterion achieves a drug discovery objective and the probability that a training compound that does not meet the selection criterion achieves the drug discovery objective.

A seventh embodiment of the invention is a computer program product for enabling a computer to analyze compound data. Computer readable program code means for receiving a data of an objective. The method continues by computer readable program code means for causing a computer to identify receiving into a memory a training data from a training data set comprising at least one training compound with at least one property value for each training compound. The method continues by computer readable program code means for causing a computer to identify receiving into a memory a data identifying each training compound as achieving an objective or not achieving the objective. The method continues by computer readable program code means for determining at least one selection criteria for each of at least one of the properties in the training data set, each of the selection criteria corresponding to a property value or range of property values, such that those training compounds in the training data set which meet the selection criteria have a higher probability of meeting the objective than the average of the training compounds in the training data set. The method continues by computer readable program code means for determining an importance value for each selection criterion.

An eighth embodiment of the invention is a computer program product for enabling a computer to analyze compound data. The eighth embodiment optionally utilizes a step of providing data of an objective to the memory. The method continues by computer readable program code means for receiving a training data from a training data set comprising at least one training compound with at least one property value for each training compound. The method continues by computer readable program code means for receiving a data identifying each training compound as achieving an objective or not achieving the objective. The method continues by computer readable program code means for defining a box in the space of properties containing all of the training compounds in the training data set. The method continues by computer readable program code means for performing one or more peeling steps, removing a proportion of the training compounds $\gamma$, with $\gamma$ can take a value greater than zero and less than 0.5. The method continues by computer readable program code means for performing zero or more pasting steps, adding back a proportion of the training compounds $\beta$, with $\beta$ can take a value greater than 0 and less than 0.5. The method continues by computer readable program code means for receiving determining the selection criteria corresponding to the boundaries of the resulting box. The method continues by computer readable program code means for receiving removing the training compounds in the box from the training data set; and the method continues by computer readable program code means for running a program executable code repeating the readable code means of steps d through g until a stopping condition has been met.

A ninth embodiment of the invention is a computer program product for enabling a computer to analyze compound data. The ninth embodiment optionally utilizes a step of providing data of an objective to the memory. The method continues by computer readable program code means for receiving data from a training data set comprising at least one training compound with at least one property value for each training compound. The method continues by computer readable program code means for receiving a data identifying each training compound as achieving an objective or not achieving the objective. The method continues by computer readable program code means for defining a box in the space of properties containing all of the training compounds in the training data set. The method continues by computer readable program code means for performing one or more peeling steps, removing a proportion of the training compounds $\gamma$, with $\gamma$ can take a value greater than zero and less than 0.5. The method continues by computer readable program code means for performing zero or more pasting steps, adding back a proportion of the training compounds $\beta$, with $\beta$ can take a value greater than 0 and less than 0.5. The method continues by computer readable program code means for determining the selection criteria corresponding to the boundaries of the resulting box. The method continues by computer readable program code means for removing the training compounds in the box from the training data set. The method continues by computer readable program code means for repeating processing steps (e.g., iterating calculations, program executable code or logic) until a stopping condition has been met. The method continues by computer readable program code means for determining an importance value for each selection criterion. The method continues by computer readable program code means for receiving data from a test data set comprising at least one test compound and at least one property value for each test compound, with at least one test compound having a property which can be compared to a property of a training compound having a value present in the training data set. The method continues by computer readable program code means for applying one or more of the selection criteria to identify test compounds that meet the selection criteria. The computer program product of the ninth embodiment can optionally utilize a step in which the objective is a drug discovery objective. The computer program product of the ninth embodiment can continue with the computer readable program code means for determining an importance value for each selection criterion further use the steps of a computer readable program code means for computer outputting the selection criteria and corresponding importance values reflecting the importance of each criterion and a computer readable program code means for receiving into the memory a user input to modify the selection criteria and/or importance value of one or more selection criterion. The method of the ninth embodiment can further use the steps of a computer readable program code means for outputting at least one value for each test compound in the test set, indicating those test compounds most likely to meet the drug discovery objective. The computer program product of the ninth embodiment can further use the step of a computer readable program code means for running a program executable code calculating the importance of each selection criterion by determining the ratio between the probability that a training compound meeting a selection criterion achieves the objective and the probability that a training compound that does not meet the selection criterion achieves the objective. The computer program product of the ninth embodiment can further use the step of a computer readable program code means for outputting at least one value for each test compound in the test set, and a computer readable program code means for running a program executable code indicating those test compounds most likely to meet an objective, or optionally a drug discovery objective. The method of the ninth embodiment further uses the steps of a computer readable program code means for running a program executable code calculating the importance of each selection criterion by determining the ratio between the probability that a training compound meeting a selection criterion achieves a drug discovery objective and the probability that a training compound that does not meet the selection criterion achieves the drug discovery objective.

A tenth embodiment of the invention is a computer system adapted to analyze compound data. A computer having a memory. The tenth embodiment optionally utilizes a step of providing data of an objective to the memory. The method continues by a memory storing an objective. The method continues by a memory storing a training data from a training data set comprising at least one training compound with at least one property value for each training compound. The method continues by a memory storing a data identifying each training compound as achieving an objective or not achieving the objective. This embodiment of the method employs a step in which the computer can run program executable code determining at least one selection criteria for each of at least one of the properties in the training data set, each of the selection criteria corresponding to a property value or range of property values, such that those training compounds in the training data set which meet the selection criteria have a higher probability of meeting the drug discovery objective than the average of the training compounds in the training data set. This embodiment of the method employs a step in which the computer can run the program executable code determines an importance value for each selection criterion.

An eleventh embodiment of the invention is a computer system adapted to analyze compound data. A computer having a memory. The eleventh embodiment optionally utilizes a step of providing data of an objective to the memory. The method continues by a memory storing a training data from a training data set comprising at least one training compound with at least one property value for each training compound. The method continues by a memory storing a data identifying each training compound as achieving an objective or not achieving the objective. This embodiment of the method employs a step in which the computer can run a program executable code on the training data set defining a box in the space of properties containing all of the training compounds in the training data set. This embodiment of the method employs a step in which the computer can run a program executable code performing one or more peeling steps, removing a proportion of the training compounds $\gamma$, with $\gamma$ can take a value greater than 0 and less than 1. This embodiment of the method employs a step in which the computer can run a program executable code performing zero or more pasting steps, adding back a proportion of the training compounds $\beta$, with $\beta$ can take a value greater than 0 and less than 1. This embodiment of the method employs a step in which the computer can run a program executable code determining the selection criteria corresponding to the boundaries of the resulting box. This embodiment of the method employs a step in which the computer can run a program executable code removing the training compounds in the box from the training data set and the method continues by computer readable program code means for running a program executable code repeating the readable code means of processing steps (e.g., program code means for iterating calculations) until a stopping condition has been met.

A twelfth embodiment of the invention is a method for enabling a computer to analyze compound data. This embodiment utilizes the step of transmitting computer readable program code to a computer. The method continues by computer readable program code and means for receiving data of an objective. The method continues by computer readable program code means for causing a computer to identify receiving into a memory a training data from a training data set comprising at least one training compound with at least one property value for each training compound. The method continues by computer readable program code means for causing a computer to identify receiving into a memory a data identifying each training compound as achieving an objective or not achieving the objective. The method continues by computer readable program code means for determining at least one selection criteria for each of at least one of the properties in the training data set, each of the selection criteria corresponding to a property value or range of property values, such that those training compounds in the training data set which meet the selection criteria have a higher probability of meeting the objective than the average of the training compounds in the training data set; and the method continues by computer readable program code means for determining an importance value for each selection criterion.

A thirteenth embodiment of the invention is a method for enabling a computer to analyze compound data. This embodiment utilizes the step of transmitting computer readable program code to a computer. The thirteenth embodiment optionally utilizes a step of providing data of an objective to the memory. The method continues by computer readable program code means for receiving a training data from a training data set comprising at least one training compound with at least one property value for each training compound. The method continues by computer readable program code means for receiving a data identifying each training compound as achieving an objective or not achieving the objective. The method continues by computer readable program code means for defining a box in the space of properties containing all of the training compounds in the training data set. The method continues by computer readable program code means for performing one or more peeling steps, removing a proportion of the training compounds $\gamma$, with $\gamma$ can take a value greater than 0 and less than 1. The method continues by computer readable program code means for performing zero or more pasting steps, adding back a proportion of the training compounds $\beta$, with $\beta$ can take a value greater than 0 and less than 1. The method continues by computer readable program code means for receiving determining the selection criteria corresponding to the boundaries of the resulting box. The method continues by computer readable program code means for receiving removing the training compounds in the box from the training data set; and the method continues by computer readable program code means for running a program executable code repeating the readable code means of processing steps (e.g., program code means for iterating calculations) until a stopping condition has been met.

A fourteenth embodiment of the invention is a computer useable medium having computer readable instructions stored thereon for execution by a computer processor to perform analysis of compound data. This embodiment utilizes the step of providing a computer having a memory. The fourteenth embodiment optionally utilizes a step of providing data of an objective to the memory. This embodiment of the method in a step provides to the memory a training data from a training data set comprising at least one training compound with at least one property value for each training compound. This embodiment of the method in a step provides to the memory a data identifying each training compound as achieving an objective or not achieving the objective. This embodiment of the method employs a step in which the computer can run program executable code on the training data set. This embodiment includes a method step in which the program executable code can determine at least one selection criteria for each of at least one of the properties in the training data set, each of the selection criteria corresponding to a property value or range of property values, such that those training compounds in the training data set which meet the selection criteria have a higher probability of meeting the objective than the average of the training compounds in the training data set. This embodiment includes a method step in which the program executable code can determine an importance value for each selection criterion.

A fifteenth embodiment of the invention is a computer useable medium having computer readable instructions stored thereon for execution by a computer processor to perform analysis of compound data. This embodiment utilizes the step of providing a computer having a memory. The fifteenth embodiment optionally utilizes a step of providing data of an objective to the memory. This embodiment of the method in a step provides to the memory a training data from a training data set comprising at least one training compound with at least one property value for each training compound. This embodiment of the method in a step provides to the memory a data identifying each training compound as achieving an objective or not achieving the objective. The method continues by the computer can run a program executable code on the training data set defining a box in the space of properties containing all of the training compounds in the training data set. The method continues by the computer can run a program executable code performing one or more peeling steps, removing a proportion of the training compounds $\gamma$, with $\gamma$ can take a value greater than 0 and less than 1. The method continues by the computer can run a program executable code performing zero or more pasting steps, adding back a proportion of the training compounds $\beta$, with $\beta$ can take a value greater than 0 and less than 1. The method continues by the computer can run a program executable code determining the selection criteria corresponding to the boundaries of the resulting box. The method continues by the computer can run a program executable code removing the training compounds in the box from the training data set. The method continues by the computer can run a program executable code repeating processing steps (e.g., iterating calculations, program executable code or logic) until a stopping condition has been met.

DETAILED DESCRIPTION OF THE INVENTION

Figure 1:
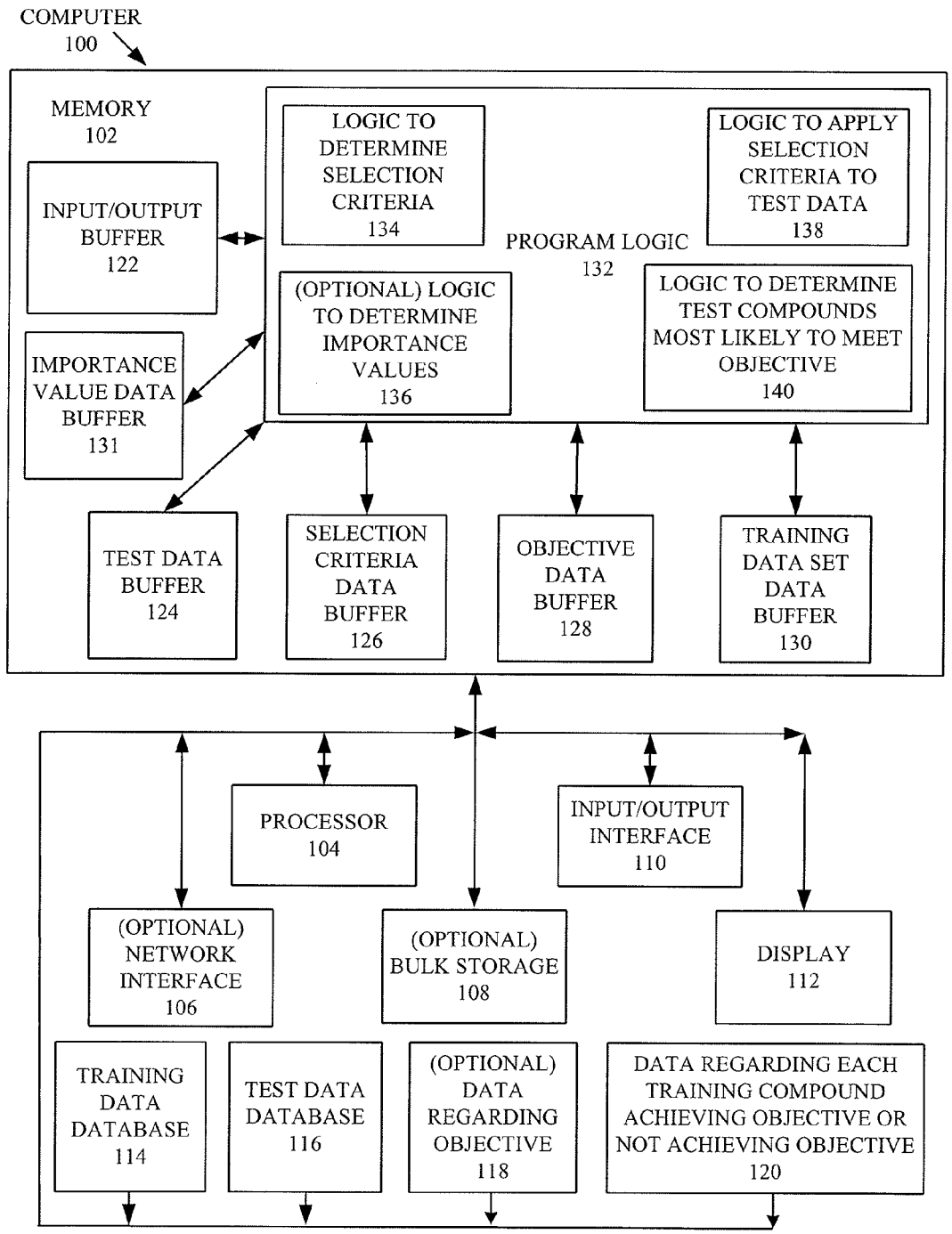
FIG. 1 is a functional block diagram of a computer system.

Embodiments of the invention disclosed herein can comprise a rigorous, automatic method for analysis of historical data to extract easily interpretable selection criteria and their importance for selection of compounds with a high likelihood of success against a drug discovery objective or other objective (collectively herein as "objective" or "objectives"). These criteria and their importance are also easily modifiable by a user to reflect a user's opinions and requirements.

Embodiments of this invention can provide an assessment of the importance of each property in determining the outcome of research. In an embodiment utilizing properties which are generated experimentally, embodiments of this invention can avoid waste by eliminating unnecessary experiments where the data such unnecessary experiments would have little impact on the selection of compounds. Embodiments of this invention can produce easily interpretable information on the importance of properties.

The research and development (R&D) of chemical compounds for use as drugs or for other applications is time consuming and expensive. The failure rate of compounds is very high and this failure often occurs late in the R&D process, after large costs have been incurred. Embodiments of this invention can comprise a method and system to 'learn' rules from historical data on the properties of compounds that help to distinguish compounds that succeeded against a R&D, or any other, objective from those that failed. These rules are expressed as selection criteria, based on property data that can be generated early in the R&D process, which can be used to select new compounds that are likely to meet the same objective, thus eliminating time, effort and money spent on compounds that are likely to fail. Furthermore, in its many embodiments selection criteria can be easily interpretable by a scientist, so that the selection criteria can be easily understood and justified or modified, if necessary, to reflect the scientist's expert opinion. Finally, embodiments of this invention can determine the importance of each selection criterion in selecting compounds that are likely to succeed against the objective. This means that unimportant selection criteria can be dropped, eliminating the need to generate the associated property data, thus further reducing cost and wasted effort.

There are many successful drugs on the market that treat a wide variety of diseases. However, in the drug discovery and development process, a much larger number of compounds are synthesised and tested that fail to become drugs because they do not have appropriate properties. For example, they can lack the appropriate pharmacological effect, not be absorbed when swallowed as a pill, they can be metabolised too quickly or they can have a toxic effect. The process of drug discovery involves the search for a candidate drug compound that can meet all of the drug discovery objectives necessary to be a suitable therapy for a given disease. The candidate drug then goes on to drug development in which it is rigorously tested in animals and, eventually, in the clinic to ensure that it is safe and has the desired therapeutic effect.

In drug discovery, data can be generated for any number of compounds and for a wide variety of properties. These property data can be used for selection of compounds to progress for further, more detailed, investigations and ultimately to select one or more candidate drugs for testing in pre-clinical and clinical development. In embodiments of this invention selection criteria can be applied to test data for selection of compounds that are likely to achieve one or more of the drug discovery objectives of a drug discovery project.

Embodiments of this invention can use a training set of training compounds with associated property values for one or more properties. Training data from a training data set based on training compounds can be utilized. The outcomes for the training compounds are known beforehand and a value can be input for each of the training compounds to identify the extent to which each training compound achieves a drug discovery objective or other objective, or does not. The system can then search for one or more selection criteria which distinguish training compounds from the set of training compounds that successfully meet or achieve an objective from those that do not. The determination of selection criteria is computed in a statistically rigorous manner. For non-limiting example, the determination of selection criteria distinguishing training compounds that meet a drug discovery objective from those that do not meet a drug discovery objective is computed in a statistically rigorous manner. The method can apply the generated selection criteria to a new set of compounds, described as a test set of test compounds, which are not in the training set. The method can determine which test compounds, i.e. those compounds that meet the selection criteria, have a higher probability of achieving the objective than test compounds that do not meet the selection criteria. Embodiments of this invention can produce selection criteria which can result in the synthesis and testing of fewer compounds that fail to meet drug discovery objectives and hence reduce the cost and time taken to discover new compounds or drugs.

The method can also compute estimates of, or directly calculate, an importance value for each selection criterion in selecting test compounds that have a high probability of achieving a drug discovery objective or other objective. The determination of the importance of a selection criterion can help to inform the decision regarding whether to generate data for the corresponding property either manually or automatically. This method can save wasted effort and cost incurred by generating data that is unimportant to selecting compounds that are likely to meet an objective. An importance value can be a number in a range between two fixed points (e.g. 0 to 1, or 0 to 10), one end of the scale reflecting an important (or even critical) criterion that can be met in order to achieve a drug discovery objective and the other reflecting a property that was unimportant to selecting compounds that are likely to meet the drug discovery objective. Alternatively, the importance value can be a classification of each criterion into one of a limited number of possible classes reflecting their importance (e.g. high, medium and low).

It is a feature of embodiments of this invention that selection criteria and importance values are easily interpretable by scientist and researchers. Such scientists can include for non-limiting example drug discovery scientists. The output of embodiments of this invention can be understood and justified by scientists. Scientists can apply the selection criteria generated by this method when considering selection of test compounds. In one embodiment, a user can modify selection criteria before they are applied to select test compounds. Such modification can result from input reflecting the expert knowledge of the scientist. Such input can be used with, instead of, or in addition to some or all of the data selection criteria or other data generated by the method.

In one embodiment the system can automatically apply selection criteria, identified from the training set and optionally modified by a user, to select test compounds from a test set with a high chance of meeting a drug discovery objective. This can automatically prioritize test compounds for further investigation that are more likely to succeed downstream and allow resources to be focused more effectively, thereby reducing cost and the number of research failures. For non-limiting example, this method can reduce the cost and number of late stage failures in drug discovery and development.

In addition to the customary and ordinary meaning of the term "molecule", herein the term is to be broadly construed to also mean "two or more atoms held together by at least one chemical bond". The chemical bond can be of any type or nature. Herein the term "compound", in addition to its customary and ordinary meaning is used synonymously with the term "molecule". Herein the term "drug" is to be broadly construed to mean, in addition to its customary and ordinary meaning, "a molecule for use to treat an illness, relieve a symptom, modify a chemical process in the body of a human or other species".

In its many embodiments, embodiments of this invention can be used to produce results for drug discovery regarding any size or complexity of compound. It is to be broadly used in research comprising in non-limiting example small molecule research (e.g., molecules with a molecular weight of <1000 Da), medium molecule research (e.g., oligonucleotides), large molecule research (e.g., vaccines, antibodies or protein therapeutics). Embodiments of this invention can also be used to produce results for other research, e.g. agrochemicals, cosmetics and medical diagnostic compounds. These examples are non-limiting and the method can be used for research of any compound. These molecules for which this method can be utilized can be of any nature and the scope of molecules includes drug compounds and non-drug compounds, organic or inorganic compounds, as well as simple and complex molecules.

Embodiments of this invention can be used for target selection or for the discovery of biological targets. The selection of a target is a decision that influences the chance of success of a pharmaceutical R&D project. This applies in non-limiting example to identifying a target for treatment of a therapeutic indication.

FIG. 1 is a functional block diagram of a computer system which performs execution of computer processes. The computer systems include a computer 100, a memory 102, a processor 104, an optional network interface 106, an optional bulk storage 108, an input/output interface 110, a display 112, and databases. The databases can compromise a training data database 114, a test data database 116, optionally a data regarding an objective 118, and data regarding each training compound achieving objective or not achieving objective 120. The computer system also includes an input/output buffer 122, a test data buffer 124, a selection criteria data buffer 126, an objective data buffer 128, a training data set data buffer 130 and an importance value data buffer 131. The computer system also includes executable code 132 which can compromise executable code to determine selection criteria 134, optionally executable code to determine importance of values 136, executable code to apply selection criteria to test data 138, and executable code to determine test compounds most likely to meet an objective 140.

Figure 2A:
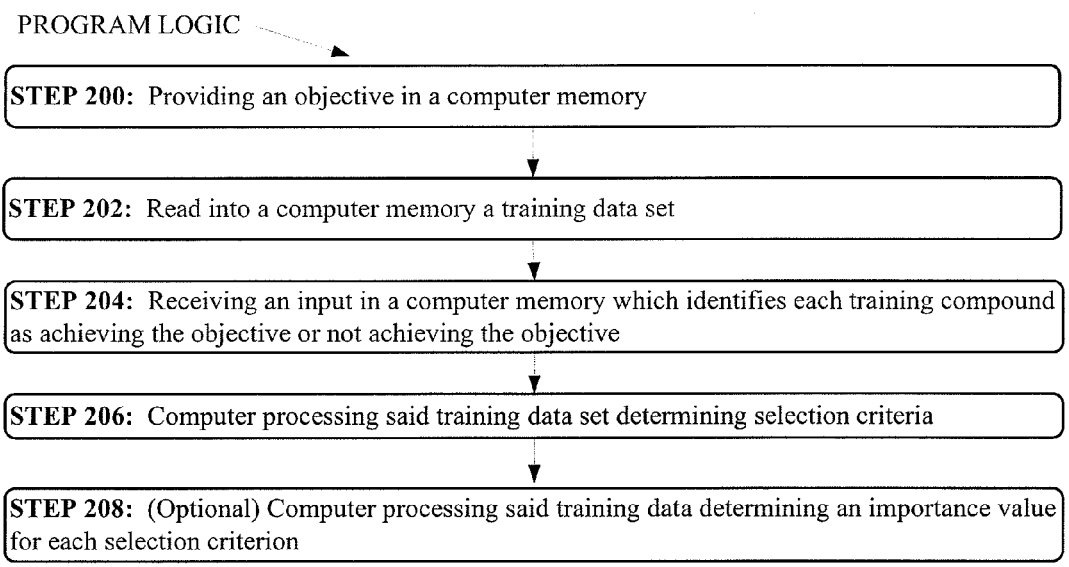
FIG. 2A is a process used for determining selection criteria from a training data set.

FIG. 2A is an embodiment of executable code for an embodiment of the method for determining selection criteria from a training data set. FIG. 2A is a flow diagram of an embodiment for a sequence of steps which can be carried out by the computer system of FIG. 1. While FIG. 2A shows the program logic having a sequence of steps, in its many embodiments, the data analysis can be implemented in different orders, sequences and/or steps. This flexibility regarding sequence can be utilized in embodiments when the data associated with a step is available in a computer memory at the time the step is executed. Thus, were data is available for computer processing, the steps can be used in various sequences and implementations.

Step 200 is providing an objective. Herein the term "objective" means a goal to be attained during the course of research and development to identify a molecule or compound for a purpose and should be broadly construed. "Objective" comprises all objectives which can be utilized with this method including in non-limiting example any drug discovery objective, any agrochemical discovery objective, any medical diagnostic compound discovery objective, any chemical industry objective, and any flavouring objective.

An objective can be regarding drug discovery or any other objective for a molecule or compound. This meaning includes in non-limiting example, a drug discovery objective, a discovery objective, a research objective, or other user objective. The objectives which can be employed with embodiments of this invention are without limitation.

An objective can include many forms. In non-limiting example, a type of a drug discovery objective can be determined based upon the stage of a drug discovery project. An objective can comprise an interim objective that can be met prior to progressing to a later stage of drug discovery or into development or the ultimate objective of identifying a compound as a candidate drug for a safe and efficacious treatment in the patient (human or animal).

In this step an objective can be determined for which to identify one or more selection criteria from a training data set.

Example objectives comprise, but are not limited to those disclosed herein. The method can employ one or more objectives. An objective of the method can be achieving acceptable potency in a cell-based assay. An objective of the method can be achieving efficacy in an animal model of the disease targeted by the project at an acceptable dose. An objective of the method can be achieving a suitable pharmacokinetic profile in an animal species, e.g. oral bioavailability, volume of distribution, half-life, or penetration of the blood-brain-barrier. An objective of the method can be a lack of toxicity at an acceptable dose in an animal species. An objective of the method can be selection as a development candidate drug. An objective of the method can be achieving an efficacy in the patient population at an acceptable dose. An objective of the method can be a suitable pharmacokinetic profile in the patient population, e.g. oral bioavailability, volume of distribution, half-life or penetration of the blood-brain-barrier. An objective of the method can be lack of side effects at an acceptable dose in the patient population.

A successful, safe and efficacious drug can satisfy multiple objectives. These examples of objectives are not to be considered limiting and the methods and embodiments of this invention are unlimited in the objectives which can be employed.

In some embodiments, an objective can be a combination of multiple sub-objectives, e.g. achieving efficacy in an animal model at a given dose and demonstrating lack of toxicity at the same dose. In non-limiting example, sub-objectives can be achieving a suitable pharmacokinetic profile and achieving acceptable activity in a cell-based assay. A non-limiting example of an embodiment using multiple sub-objectives is achieving efficacy in an animal model at a given dose and demonstrating lack of toxicity at the same dose. The utilization of objectives and sub-objectives in the embodiments of this method is considered to be without limitation and to be broadly construed.

Other objectives to which this approach would be applicable include those relating to the identification of agrochemicals, cosmetics, food flavourings or industrial chemicals. In a non-limiting example, requirements for an agrochemical such as a pesticide include effectiveness against the target pest organism, quick degradation in contact with the soil, and poor intestinal absorption if ingested by a human.

Step 202 is to read into computer memory a training data set. In Step 202 the property values $(x_{ij})$ for each training compound in the training set can be read into the computer memory. These data can be read from a machine readable medium or can be input by a user.

In the several embodiments of this method drug discovery property data can be employed from an unlimited variety of sources. Property data can be derived in many ways. It can be calculated, predicted computationally, estimated or measured experimentally, and can cover a wide range of different properties. The method can employ one or more property data and property data types. The type, variety and nature of property data employed by the embodiments of this invention are considered without limitation. Property data is to be broadly construed and are not limited to the examples disclosed herein. The following examples are intended to be non-limiting. Property data can comprise simple characteristics of a molecule, e.g. molecular weight, number of heavy atoms, counts of hydrogen bond donors and acceptors, polar surface area, number of rotatable bonds. Property data can comprise activity against a biological target(s) of interest. Property data can comprise activity against off-targets, i.e. biological targets against which activity would ideally be avoided. Property data can comprise physicochemical properties such as solubility, pKa and lipophilicity. Property data can comprise absorption, distribution, metabolism and excretion (ADME) properties measured in vitro, such as membrane permeability (e.g. permeability through Caco2 or MDCK cell lines or artificial membranes), metabolic stability in expressed enzyme systems, liver microsomes or hepatocytes, active transport activity. Property data can comprise pharamacokinetic properties, measured in vivo, such as bioavailability, clearance, half-life, volume of distribution, blood-brain-barrier penetration and concentration in target tissues. Property data can comprise toxicity properties measured in vitro, such as inhibition of the hERG ion channel, AMES mutagenicity, cytotoxicity. Property data can comprise toxicity measures in vivo, based on pathology studies following dosing of the compound of interest. Property data can comprise efficacy in animal models of the disease that is the treatment goal. Any of these example property data, or other data can be employed as a single property data, data or characteristic, or in combination and in any amount of property data from a single property data to extremely large quantities of property data as computer processing, or other technology, can process, utilize or transform.

Herein "property data" is to be broadly construed to mean, in addition to its ordinary and customary meaning, any data associated with a molecule or compound. The term "data" is used synonymously with "property data" at times herein. When not used synonymously with "property data", the term "data" in addition to its ordinary and customary meaning means "any data of any type". Both of these terms are to be broadly construed.

Property data derived from less expensive, computational or in vitro methods can be used to select compounds for studies involving the more expensive or time consuming methods, such as in vivo pharmacokinetics, efficacy or toxicity studies. This can be an iterative process, in which compounds are progresses to increasingly time consuming or expensive studies.

Sources for computationally predicted property data include, but are not limited to, Quantitative Structure Activity Relationship (QSAR) models, pharmacophore models, docking models and numerical simulations such as physiological-based pharmacokinetic models that can, in turn, take experimental property data as inputs.

Sources for experimental property data include high throughput screening, in vitro laboratory tests, cell-based assays and in vivo tests in animal models of disease, pharmacokinetics studies and toxicology studies.

Property values can be numerical or categorical. A non-limiting example of categorical values are, e.g. good/bad, or high/medium/low.

Experimental property measurements and computational property predictions can also be generated for compounds intended for other purposes, such as agrochemicals, cosmetics, flavourings or industrial chemicals.

Due to advances in high-throughput screening and computational prediction technologies the quantity of data available for utilization with this method are increasing. In the non-limiting example context of drug discovery, this can include compound-related data from the earliest stages of drug discovery. In non-limiting example such data can comprise a wide range of target activity, absorption, distribution, metabolism and excretion (ADME) properties, toxicity and predictive modelling data. In an embodiment, this method can employ any number and type of properties simultaneously to test an objective and find an appropriate research result.

The training data set can contain one or more training compounds for which the outcome of the objective is known. For each of these training compounds the values for one or more properties must also be known. These property values can have been obtained experimentally or predicted computationally.

The training data set can contain N compounds, where N is greater than or equal to one. The properties of a training compound, i ($1 \leq i \leq N$), can be represented by a vector $x_i$ containing M entries, where M is greater than or equal to one. Each entry, $x_{ij}$ ($1 \leq j \leq M$), represents one property value.

Step 204 is to identify each training compound as achieving the objective or not achieving the objective. In this step, each training compound can be assigned a label ($y_i$) indicating if each training compound meets the objective.

In one embodiment, these labels can have been previously defined by a user and can be read into the computer memory from a machine readable medium. These can be read from the same file as the compound data set or from a different file. In an alternative embodiment, the labels can be defined by input from a user.

For each training compound, i ($1 \leq i \leq N$), in the training data set, a label, $y_i$ ($1 \leq i \leq N$), can be assigned indicating if the training compound has met the objective of interest. For training compounds that meet the objective $y_i=1$; for training compounds that do not meet the objective $y_i=0$.

This approach could be further extended to allow the label yi for each training compound to take any numerical value (i.e. not limited to 0 or 1) indicating the extent to which the training compound meets the objective. The method is not limited in to a binary case and can have any level of complexity.

Step 206 is determining selection criteria. A selection criterion for a property can take one of a number of forms. For a property represented by numerical data, a selection criterion can be a threshold value and side of the threshold, for example, 'greater than 5' (>5) or 'less than 8' (<8). Optionally, such a selection criterion can include the threshold value itself, e.g. 'less than or equal to 10' ($\leq 10$) or 'greater than or equal to 2' ($\geq 2$). A selection criterion for numerical data can also indicate a range, e.g. 'between 4 and 6' (4-6) and can optionally include the boundaries of the range. For a property represented by a category or classification, a selection criterion can be a single class, e.g. 'high' or a contiguous range of classes, e.g. 'high or medium'.

A set of selection criteria is defined by a 'box' in the property space S. The property space, S, can be a Cartesian space in which each dimension represents a single property and the boundaries of the space in each dimension are defined by the maximum and minimum values of the corresponding property for a training set compound.

Here box B is defined, in the space S, as an axis-aligned box. The boundaries of the box in each dimension represent the upper and lower bounds of the range of values which meet the selection criterion for the property corresponding to that dimension:

$$B = \begin{Bmatrix} B_1 & \ldots & B_M \\ \underline{B}_1 & \ldots & \underline{B}_M \end{Bmatrix},$$

i.e. a compound, i, can meet a selection criterion for property, j, if and only if $\underline{B}_j < x_{ij} < \overline{B}_j$ or, in the case where the boundaries are considered included in the range, $\underline{B}_j \leq x_{ij} \leq \overline{B}_j$. In the case of a selection criterion represented by an unbounded range, e.g. 'greater than 5' or 'less than 8' one of the values can be infinite. For example, the selection criterion 'greater than 5' would be represented by the values $\underline{B}_j=5$ and $\overline{B}_j=\infty$.

In an embodiment of Step 206, selection criteria for one or more of the properties can be automatically determined by an algorithm implemented on a computer based on the training compound data $x_i$ and labels $y_i$.

The output of this step can be one or more sets of selection criteria on the property values, represented by boxes, $B_k$ ($1 \leq k \leq P$), where P can take any value greater than 1. Each set of selection criteria can include selection criteria for one or more of the properties of the training compounds in the training data set.

For each set of selection criteria, training compounds in the training data set that meet the criteria can have a higher probability of achieving the objective than the average probability of the training compounds in the training data set.

In a bump hunting embodiment the selection criteria are determined using an algorithm that can be described as follows:

Constructing a Single Box

A single box $B_1$ can be constructed utilizing a top-down 'peeling' process followed by a bottom-up 'pasting' procedure.

Peeling

Figure 4:
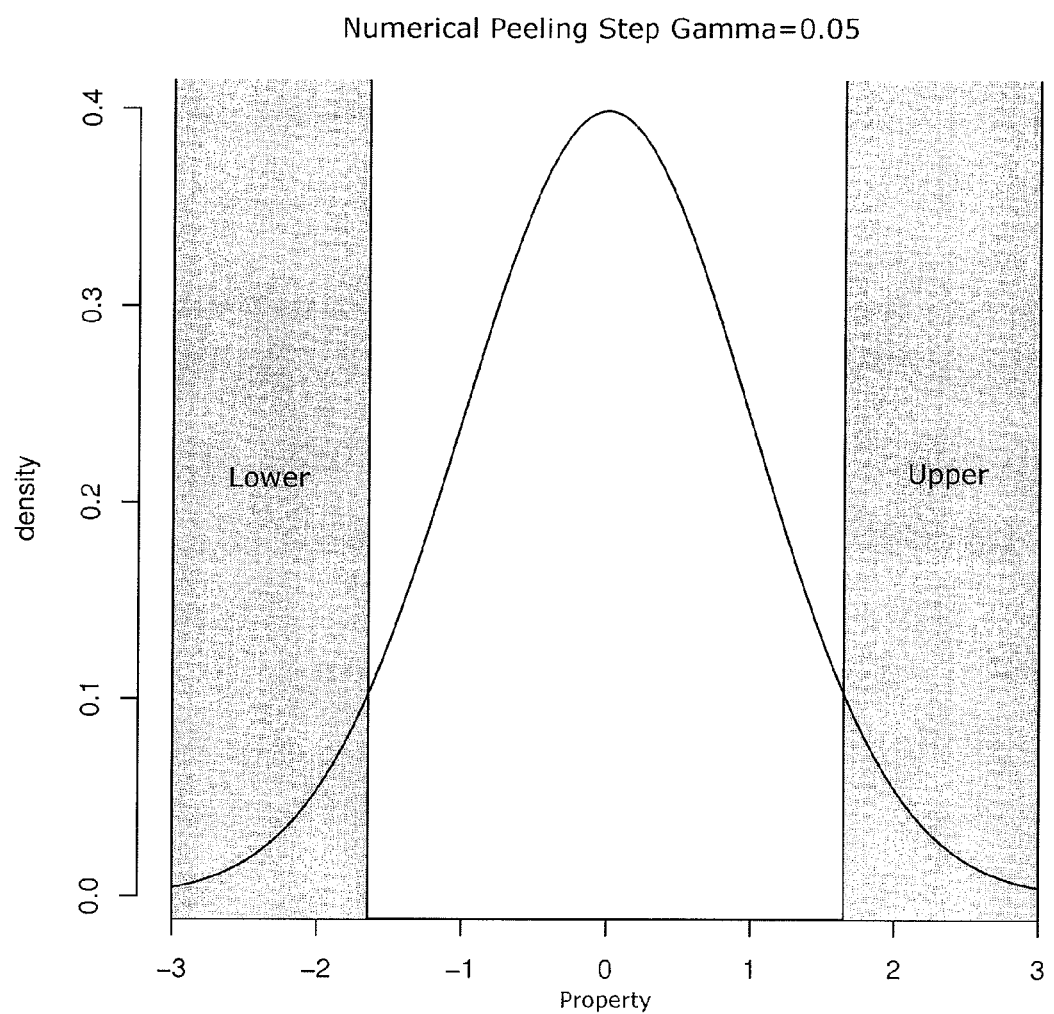
FIG. 4 is an illustration of a peeling step with peeling proportion $\gamma=0.05$.

FIG. 4 is an illustration of a peeling step with peeling proportion $\gamma=0.05$, where one of the ranges of property values shaded in grey and labelled Upper and Lower can be removed from the box.

The box construction strategy can be a top-down process called 'peeling', setting $B_1$ to be equal to the entire property space S for the training set of training compounds and remembering that each face corresponds to an upper or lower bound on an individual compound property value. At each step, the box can be compressed along a single face; the face chosen for compression is the one that can result in the largest mean $y_i^{B_1}$ in the newly compressed box $B_1$ (see FIG. 4). The process can be repeated until a predefined stopping condition (e.g. if the number of training compounds in the box $B_1$ becomes too small) is reached. Alternatively, an executable program code or a user can keep a record of each box in the peeling sequence and select the optimal box $B_1$ from the sequence using a cross validation approach.

Specifically, a single peeling step involves considering each property j in turn ($1 \leq j \leq M$):

If the jth property is numerical, the peeling step for the box $B_1$ involves considering removing either the training compounds i whose $x_{ij}$-values are below the $x_{ij}$-values' $\gamma$-quantile (with respect to property j) or those above the $(1-\gamma)$-quantile, depending on which removal can result in the higher mean for the remaining training compounds in the compressed box. Here, $\gamma$ is the 'peeling fraction' specifying how many training compounds to remove in each step. $\gamma$ can take any value in the range 0 to 1. Ranges of $\gamma$ can include in non-limiting example 0 to 0.2 or 0 to 0.5.

If the jth property is categorical, the peeling step for the box $B_1$ involves considering removing all the training compounds i whose $x_{ij}$-values are equal to one of $x_{ij}$'s possible category values, the category can be removed that can result in the highest mean for the remaining training compounds in the compressed box when removed.

After considering each property j, a final choice of the box face to compress is based on which of the above candidates for removal results in the highest mean for the remaining training compounds in the compressed box when removed.

Pasting

Figure 5:
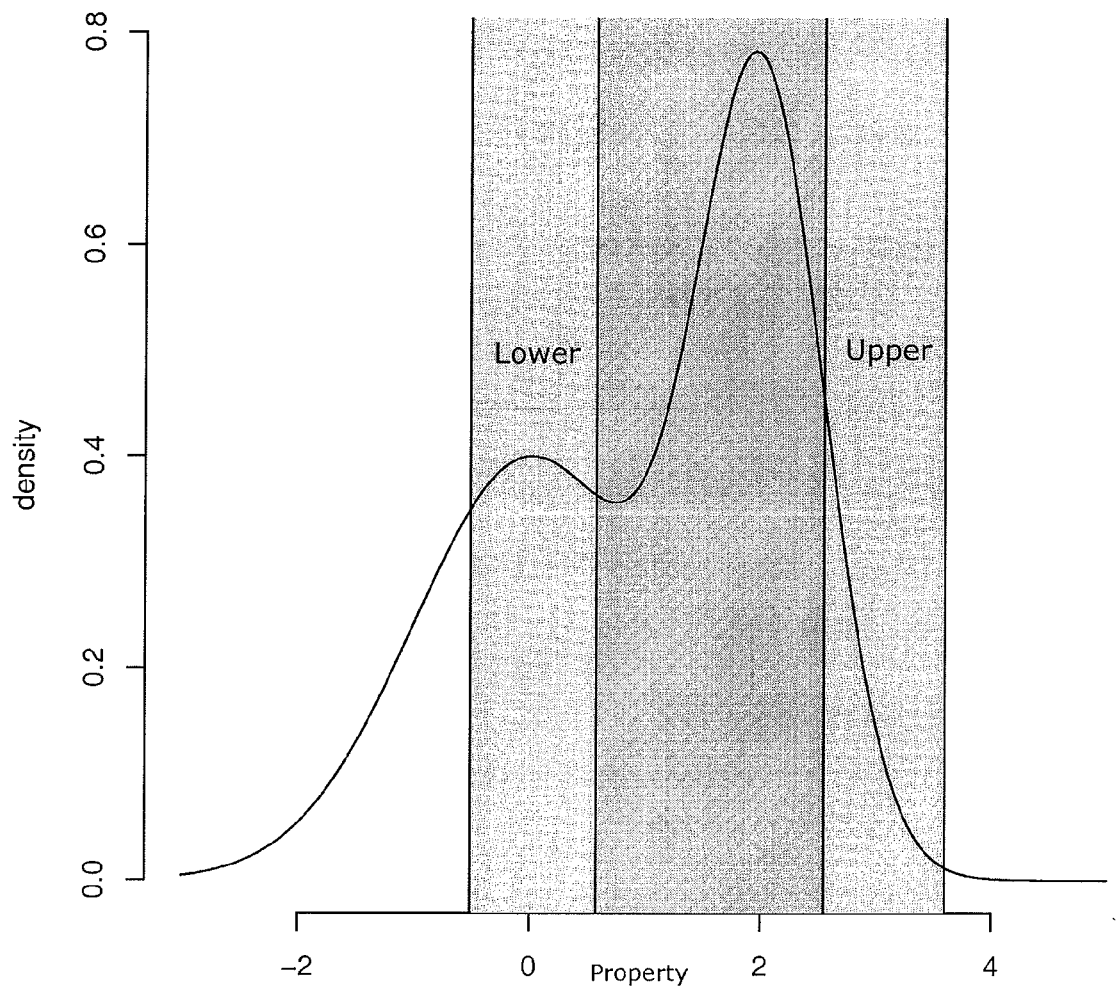
FIG. 5 is an illustration of a pasting step with pasting proportion $\beta=0.2$.

FIG. 5 is an illustration of a pasting step with pasting proportion $\beta=0.2$, where the range of property values shaded in light grey and labelled Upper and Lower can be added back to the box, shown shaded in dark grey.

Because top-down peeling greedily chooses the next face for compression, it is possible that the increase box $B_1$'s mean can be increased still further via a bottom-up 'pasting' strategy; this is essentially the inverse of the top-down peeling process. The box $B_1$ can be iteratively expanded along whichever face results in the largest increase in the mean $y_i^{B_1}$, stopping when the next expansion will result in a decrease in the box mean (see FIG. 5).

Specifically, a single pasting step involves considering each property j in turn ($1 \leq j \leq M$):

If the jth property is numerical, the pasting step proceeds by considering extending either the lower or upper boundary of $B_1$ on the jth property, thus adding $\beta N_{B_1}$ of the previously peeled training compounds to the box $B_1$ where $\beta$ is the 'pasting fraction' and $N_B$ is the number of training compounds in $B_1$. $\beta$ can take any value in the range 0 to 1. Ranges of $\beta$ can include in non-limiting example 0 to 0.2 or 0 to 0.5.

If the jth property is categorical, pasting proceeds by considering adding the training compounds i whose $x_{ij}$-values are equal to one of the categories for property j not represented in the current box $B_1$, the category can be added that can result in the highest mean for the new set of training compounds in the expanded box when added.

After considering each property j, a final choice of the box face to expand is based on which of the above candidates for addition results in the highest mean for the new set of training compounds in the expanded box when added.

Constructing a Set of Boxes

As a result of the top-down peeling process followed by bottom-up pasting, a result can be a single box $B_1$ with a high target mean $y_i^{B_1}$. The procedure can be started again with the entire property space minus the training compounds from box $B_1$ (i.e. $S-B_1$) to get a second box $B_2$, and repeat this process to generate P boxes. The final result can be a 'covering' of boxes $B_1, \ldots, B_P$ that collectively describes the region of the property space where the mean of $y_i$ is large.

Stopping Condition

The box construction process can continue until the process reaches a stopping condition. A stopping condition can occur when a box $B_{P+1}$ is constructed that has a mean, $y_i^{B_{P+1}}$, less than a predefined value or with a number of training compounds in that box below a pre-specified value. Values for a stopping condition on $y_i^{B_{P+1}}$ can take any value greater than zero and less than one and typical values can be in the range 0.4-0.6. Values for a stopping condition on the number of training compounds in box $B_{P+1}$ can take any value greater than zero and less than the number of training compounds in the training data set and typical values can be in the range 1 to 20% of the total number of training compounds in the training data set.

Step 208 is an optional step to determine an importance value for each selection criteria. In this step, an importance value can be determined for each selection criterion in each set of selection criteria reflecting the importance of that selection criterion in distinguishing compounds that have a high probability of meeting the objective from those with a lower probability. Here the importance value determined for the selection criterion for property j in box k can be designated as $\lambda_{jk}$ (where $1 \leq j \leq M$ and $1 \leq k \leq P$).

In one embodiment, $\lambda_{jk}$ can be a number within a limited range, for example 0 to 1, 0 to 10 or a percentage. A value at one end of the range can represent an unimportant selection criterion and a value at the opposite end can represent an important (or even critical) selection criterion that can be met.

In an alternative embodiment, this value can take the form of a classification of each selection criterion within a limited number of classes that reflect different levels of importance.

In another embodiment a probability density estimation method can be employed (herein "probability density estimation embodiment"), wherein the importance of each selection criterion is calculated by determining the ratio between the probability that a training compound meeting a selection criterion achieves the objective and the probability that a compound that does not meet the selection criterion achieves the objective, as follows:

Let $h_{jk}(x_{ij})$ be the indicator function for whether the training compound property value $x_{ij}$ lies within the box $B_k$, so that a user can define an overall classification function can be defined as $g_k(x_i)=\Pi_j h_{jk}(x_{ij})$.

In a probability density estimation embodiment $h_{jk}(x_{ij})$ can be generalized to $\overline{h}_{jk}(x_{ij})$ so that instead of being a zero-one indicator, $\overline{h}_{jk}(x_{ij})$ is the $\alpha_j$-one indicator defined by $$\overline{h}_{jk}(x_{ij}) = \begin{cases} 1 & \underline{B_{jk}} \leq x_{ij} \leq \overline{B_{jk}} \\ \alpha_j & \text{otherwise} \end{cases}$$

Figure 6:
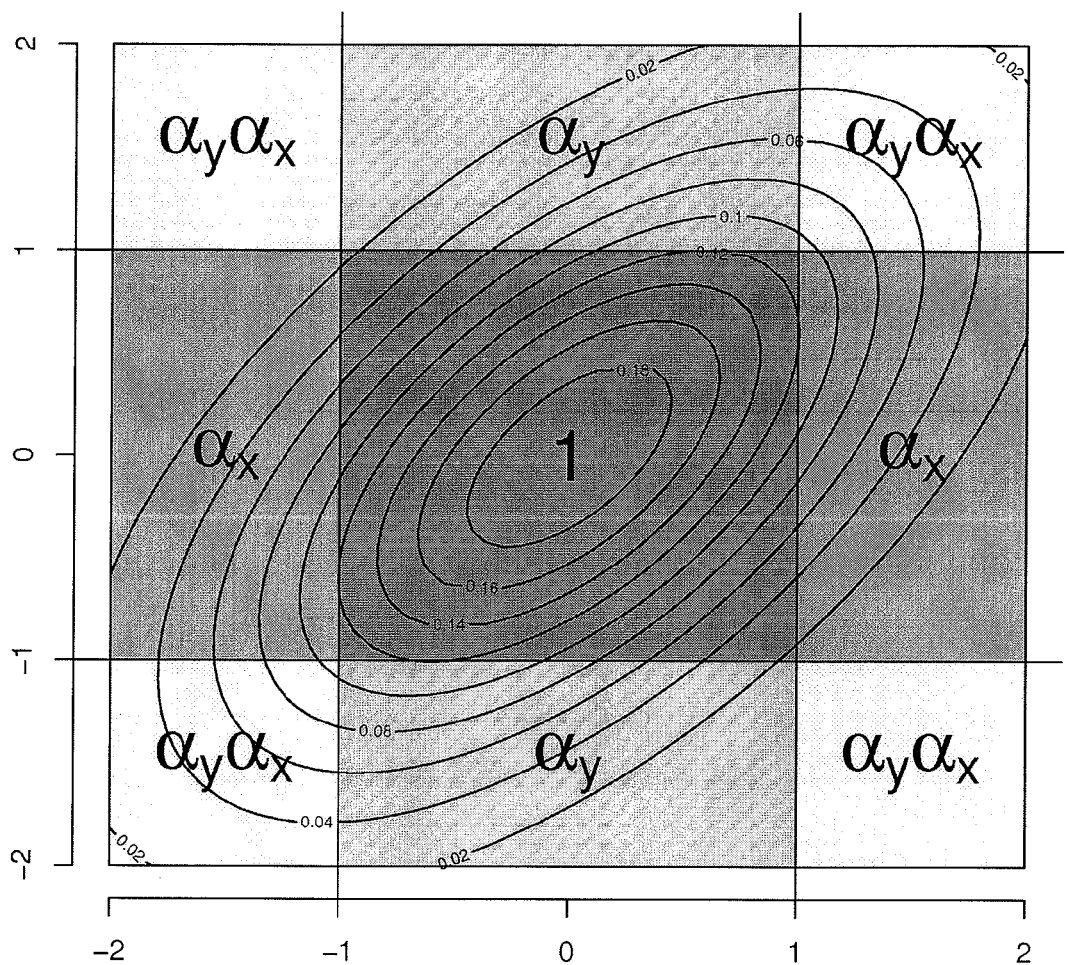
FIG. 6 is a two-dimensional illustration of the calculation of importance values.

The constant $\alpha_j$ can be interpreted as the false-negative rate of the classifier, i.e. the probability that a training compound with a property value outside of a chosen selection criterion boundary does in fact satisfy the objective (see FIG. 6).

The generalization of $h_{jk}(x_{ij})$ to $\overline{h}_{jk}(x_{ij})$ leads to an associated generalization of $g_k$ to $\overline{g}_k(x_i)=\Pi_j \overline{h}_{jk}(x_{ij})$. The function $\overline{g}_k$ defines a likelihood over the sets of values $X=\{x_1, \ldots, x_N\}$ and $Y=\{y_1, \ldots, y_N\}$:

$$L_k(X, Y) = \prod_{(i,j) \in \{h_{jk}(x_i)=0\}} \alpha_j^{y_i}(1-\alpha_j)^{1-y_i}$$

Note that the function L is convex in $\alpha_j$ and this optimization is tractable. Thus the selection criteria importance values can be determined as a principled constrained maximum likelihood optimization performed over the full set of training compounds.

For each compound i with property values $x_i$, a vector of $h_{jk}(x_{ij})$-indicators can be defined specifying whether the compound property value $x_{ij}$ lies within the box $B_k$. If the selection criteria are non-degenerate, then the probability that a particular compound i, with property values $x_i$, satisfies the objective of interest—i.e. $P(y_i=1|x_i)$—is a monotonically decreasing function of $h_{jk}(x_{ij})$. Furthermore, if a user adds the restriction that $P(y_i=1|x_i)=1$ is specified in the probability density estimation embodiment when all relevant conditions are fulfilled, the generalized classifier $\overline{g}_k$ is actually the constrained maximum likelihood estimate, $\overline{g}_k(x_i) \approx P(y_i=1|x_i)$.

In the probability density estimation embodiment, the desired selection criterion importance $\lambda_{jk}$ is equal to $1-\alpha_j$, and represents the probability that applying a certain rule would lead to a compound being mistakenly rejected—analogous to the power of a statistical test. Importantly, $\lambda_{jk}$ as defined above is correlation corrected, so that given two highly correlated variables, the one with higher explanatory power can have high importance and the other can have low importance (as it has low residual explanatory power).

Figure 2B:
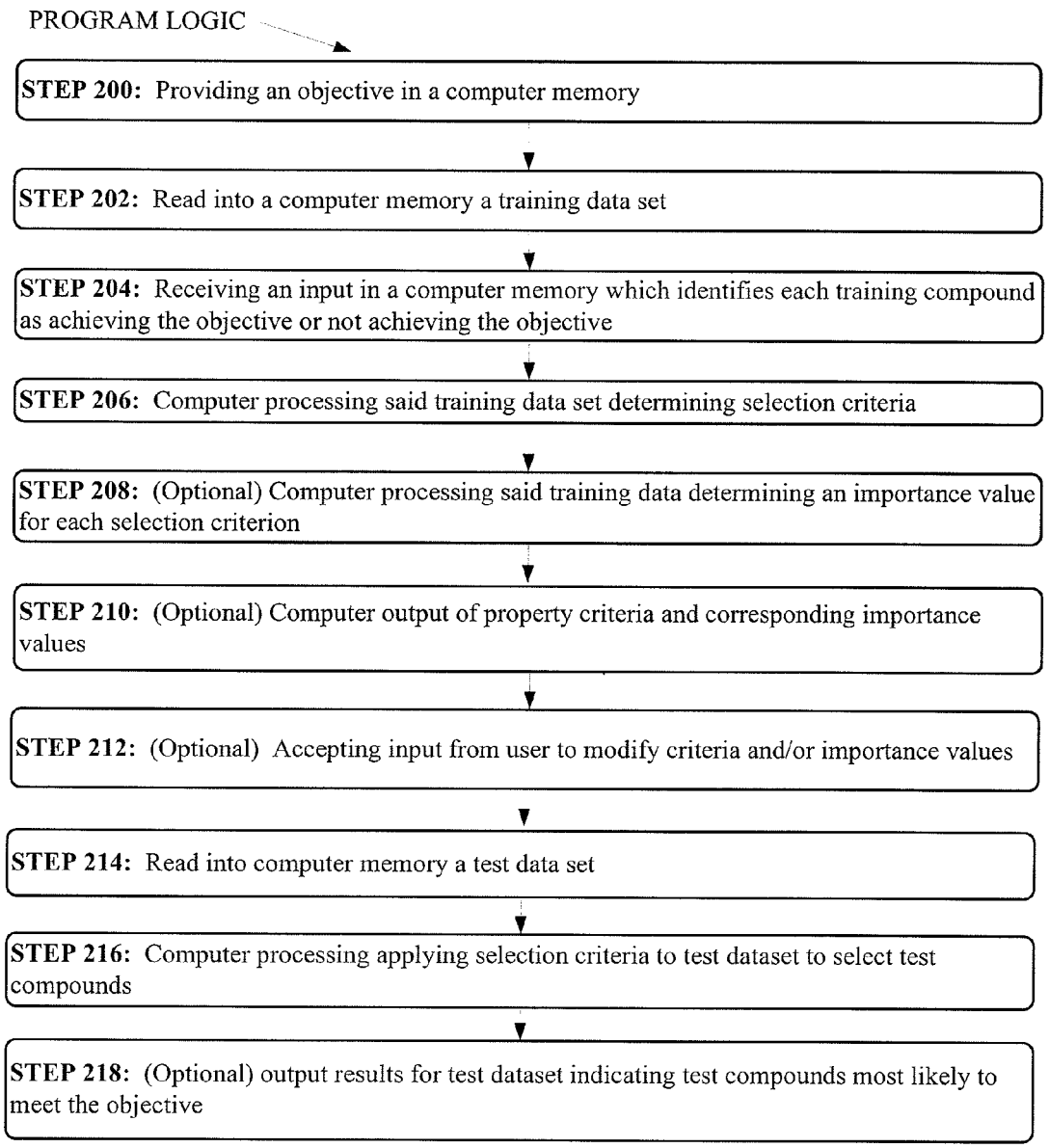
FIG. 2B is a process used for selecting test compounds from a test set.

FIG. 2B is a flow diagram of an embodiment of a sequence of steps which can be carried out by the computer system of FIG. 1. FIG. 2B is a process used for selecting test compounds from a test set based on selection criteria determined from a training set.

FIG. 2B illustrates an embodiment of program logic for the method for selection of test compounds from a test data set. Program logic can be run on the computer by program executable code. Such program executable code achieves the computer execution (running, or operation) of programming (e.g., hardware and/or software programming) on the computer to automatically conduct the program logic as disclosed herein. The method steps illustrated in FIG. 2B include method steps 200, 202, 204, 206 and 208 also illustrated in FIG. 2A and additionally illustrates method steps 210, 212, 214, 216 and 218. In an embodiment of the method, steps, i.e., 200, 202, 204, 206 and 208 are the same as for the process to identify the selection criteria from the training data set as discussed below. While FIG. 2B shows the program logic having steps, the embodiments of this invention are in no way limited to any specific sequence of operation. In its many embodiments, the data analysis can be implemented in different orders.

Step 200 is providing an objective.

Step 202 is to read into computer memory a training data set.

Step 204 is to identify each training compound as achieving the objective or not achieving the objective.

Step 206 is determining selection criteria.

Step 208 is an optional step to determine an importance value for each selection criterion.

Figure 3:
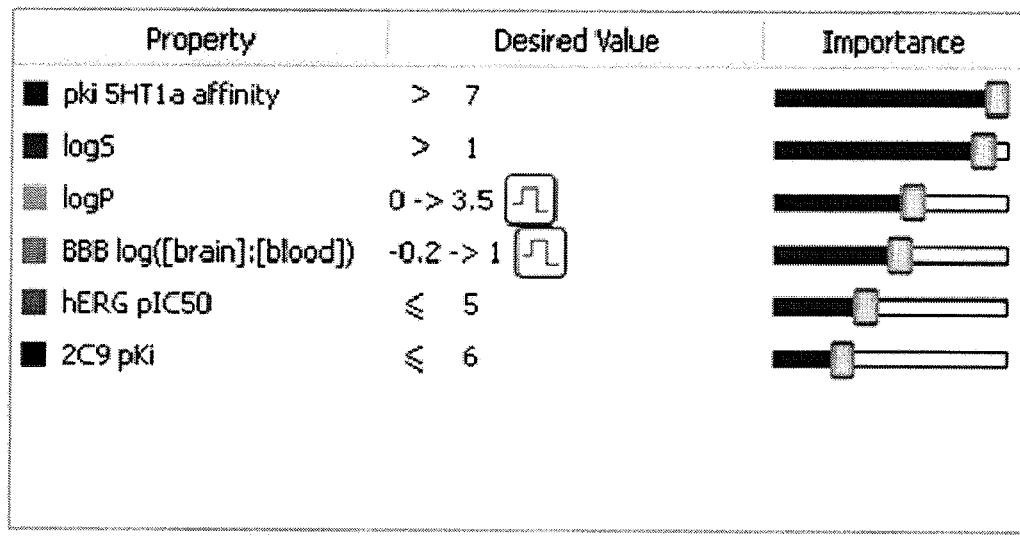
FIG. 3 is an example output of selection criteria and importance values.

Step 210 is optionally outputting selection criteria and corresponding importance values. In this step, the selection criteria and, if determined, the corresponding importance values can be output in a form that can be easily interpreted by a user. This method can provide selection criteria and their corresponding importance values represented in a form that can be easily interpretable by a user. One example of such an output is shown in FIG. 3. FIG. 3 is a non-limiting example output of selection criteria and importance values. The nature of the output of embodiments of this invention is without limitation. FIG. 3 illustrates an embodiment of a representation of output selection criteria and corresponding importance values which can be optionally employed.

Embodiments of this invention can provide high interpretability of result and a model linking properties to an outcome. This is particularly true when trying to relate individual properties to an objective. It provides an answer regarding whether a compound is likely to achieve the objective; if it is not, it can provide guidance on the properties that can be changed in order to increase the chance of achieving the objective. The method disclosed herein provides easily interpretable selection criteria for compound selection and importance values for those selection criteria. This allows experts to assess the selection criteria and, if necessary, modify these according to their experience and knowledge. In one embodiment, the method can employ a combination of rigorous, exhaustive analysis of historical data.

Step 212 is optionally accepting input from a user to modify a criteria and/or an importance value. It can be desirable for a user to modify the selection criteria and/or importance values according to their opinions based on their experience or knowledge. In this way, the process can combine knowledge gained automatically by machine learning with expert knowledge to refine the criteria by which test compounds are selected.

Modification of the selection criteria can involve modification of the upper or lower bounds of the selection criteria for one or more properties in one or more sets of selection criteria.

Modification of the importance values can involve modifying the importance values of one or more selection criteria (if calculated) in one or more sets of selection criteria. An importance value can be changed to any value within the range of acceptable numerical values or valid class for an importance value.

Step 214 is reading into computer memory a test data set. In this step the property values ($x'_{nm}$) of the test compounds in the test data set can be read into the computer memory. These data can be read from a machine readable medium or input by a user.

The test data set can contain one or more test compounds for which the outcome of the objective is unknown (Note that for validation purposes it can be desirable to apply this process to a set of compounds for which the results against the objective are known). For each of these test compounds the values for one or more properties must also be known. These property values can have been obtained experimentally or predicted computationally.

Data for at least one of the properties represented in the training data set must also be represented for the test compounds in the test data set. It is possible that some property values for test compounds in the test data set can be missing.

The test data set can contain N' compounds, where N' is greater than or equal to one.

The properties of a test compound, n (1≤n≤N') can be represented by a vector $x'_n$ containing M' entries, where M' is the number of properties represented in both the training and test data sets and is greater than or equal to one. Each entry, $x'_{nm}$ (1≤m≤M'), represents one property value of a test compound.

Step 216 is applying selection criteria to a test data set to select test compounds. In this step, one or more of the sets of selection criteria are applied to the test compounds in the test data set to identify those test compounds that are likely to meet the objective.

In a first embodiment, this can be achieved by calculation of an indicator value for each test compound and set of selection criteria, $g_k(x'_n)$ (for 1≤n≤N' and 1≤k≤P), which can take the value 1 if compound n meets all of the criteria in the set of criteria k and can take the value 0 otherwise. This can be calculated in the following way $$g_k(x'_n) = \prod_m h_{mk}(x'_{nm})$$

In this case, if a property value is missing for a test compound for one or more of the properties for which a selection criterion is defined, a third value can be assigned indicating an unknown outcome for that test compound.

In other embodiments, where the importance value for each selection criterion in a set have been calculated, a generalised score value, $\overline{g_k}(x'_n)$ (for 1≤n≤N' and 1≤k≤P), can be calculated for each test compound, n, and set of selection criteria, k, indicating the test compound's performance against the set of selection criteria. Examples include, but are not limited to:

$$\overline{g_k}(x'_n) = \sum_{j=1}^{M'} \lambda_{jk} h_{jk}(x'_{nj})$$

$$\overline{g_k}(x'_n) = \frac{1}{P} \sum_{j=1}^{M'} \lambda_{jk} h_{jk}(x'_{nj})$$

$$\overline{g_k}(x'_n) = \prod_{j=1}^{M'} \lambda_{jk} h_{jk}(x'_{nj})$$

$$\overline{g_k}(x'_n) = \sqrt[P]{\prod_{j=1}^{M'} \lambda_{jk} h_{jk}(x'_{nj})}$$

In a probability density estimation embodiment, the importance values for the selection criteria are calculated by determining the ratio between the probability that a training compound meeting a selection criterion achieves the objective and the probability that a training compound that does not meet selection criterion achieves the objective. FIG. 6 is a two-dimensional illustration of the calculation of importance values by calculating the odds ratio between a training compound meeting the selection criteria and a training compound that does not meet the selection criteria. In this embodiment, the selection criteria and corresponding importance values can be applied to calculate the odds ratio of a test compound achieving the objective, relative to a compound meeting all of the selection criteria:

$$\overline{g_k}(x'_n) \prod_{j=1}^{M'} \overline{h}_{jk}(x'_{nj})$$

In a further embodiment, where information is available on the uncertainties in the data for the property values for the test compounds in the test data set, this can be generalised to take into account the probabilities that the test compound meets each of the selection criteria and also estimate the uncertainty in the score for each test compound and each set of selection criteria.

In a further embodiment, the scores or indicator values for each set of selection criteria can be combined into a single score, $G(x'_n)$, for each test compound. Examples include, but are not limited to:

$$G(x'_n) = \sum_{k=1}^{P} \overline{g_k}(x'_n)$$

$$G(x'_n) = \prod_{k=1}^{P} \overline{g_k}(x'_n)$$

$$G(x'_n) = \max_{k=1 \ldots P}(\overline{g_k}(x'_n))$$

$$G(x'_n) = \min_{k=1 \ldots P}(\overline{g_k}(x'_n))$$

Test compounds can be selected on the basis of the indicator variable, $g_k(x'_n)$, or score, $\overline{g_k}(x'_n)$, for one or more sets of selection criteria or on the basis of an overall score, $G(x'_n)$. Examples include, but are not limited to: All test compounds with an indicator variable $g_k(x'_n)=1$ for one or more selection criteria can be selected; test compounds with a score or overall score above a threshold value can be selected; and a proportion of test compounds with the highest scores or overall scores can be selected.

Step 218 can be optionally to output results for test data set indicating test compounds most likely to meet the objective. In Step 218 the results for each test compound in the test data set are output for a user to view and apply.

Figure 7:
FIG. 7 is an example output of test compound scores.

Other embodiments include one or more lists of all test compounds that are predicted to meet one or more set of selection criteria can be output to the display screen or stored in a file on a machine readable medium, either with or without associated property values. In other embodiments, at least one list of all test compounds with at least one score or indicator variable can be output to the display screen or stored in at least one file on a machine readable medium, either with-or-without associated property values. FIG. 7 illustrates is an example output of test compound scores with associated property values.

Other embodiments include those in which the steps in FIG. 2B are executed in a different order. For example, step 14, "Reading into memory a test data set" can occur earlier in the process, for example immediately preceding or after step 202, "Reading into memory a training data set".

EXAMPLES

In these examples, set forth herein, three data sets have been utilized: "Oral_F", "Drug_data" and "Aquatic_tox".

Oral_F contains 603 compounds for which the human oral bioavailability has been measured in the clinic.

Drug_data contains 1191 compounds approved by the FDA for human administration. These compounds have been labelled as 'oral' if they are approved for oral administration or 'non-oral' otherwise. The compounds have also been labelled as 'CNS' if they can be used for treatment of a condition for which the target is in the Central Nervous System (CNS) or 'non-CNS' if their target lies outside of the CNS. Drug_data is typical of the type of 'noisy' data set which is often used to find criteria in drug discovery, as quantitative data are often not available. For example, a compound that is intended for a non-CNS target can, in practice, penetrate into the CNS, even if this is not necessary for its therapeutic effect. Therefore, clear distinctions cannot always be made between the classes of compounds.

Aquatic_tox contains 644 industrial organic compounds for which the 50% inhibitory growth concentration in mg/l ($IGC_{50}$) of each compound has been determined against the ciliated protozoan *Tetrahymena pyriformis*. This is a commonly used test for aquatic toxicity of a compound. In this data set, a compound has been labelled as having 'high' toxicity if the $IGC_{50}$ is greater than or equal to 1 mg/l and having 'low' toxicity otherwise.

The following properties were included in each of the data sets Oral_F, Drug_data and Aquatic_tox: log P—Logarithm of the octanol: water partition coefficient; MW—Molecular weight; HBD—Count of hydrogen bond donors as defined by Lipinski (Lipinski, C. A., F. Lombardo, B. W. Dominy, and P. J. Feeney. "Experimental and computational approaches to estimate solubility and permeability in drug discovery and development settings." Adv. Drug Deliv. Rev. 23 (1997): 3-25); HBA—Count of hydrogen bond acceptors as defined by Lipinski (Lipinski, C. A., F. Lombardo, B. W. Dominy, and P. J. Feeney. "Experimental and computational approaches to estimate solubility and permeability in drug discovery and development settings." Adv. Drug Deliv. Rev. 23 (1997): 3-25.); TPSA—Topological polar surface area as calculated with the algorithm by Ertl (Ertle, P, B Rohde, and P Selzer. "Fast Calculation of Molecular Polar Surface Area as a Sum of Fragment-Based Contributions and Its Application to the Prediction of Drug Transport Properties." J. Med. Chem. 43 (2000): 3714-7); Flex—The number of rotatable bonds as a proportion of the total number of bonds; Rotatable bonds—The number of rotatable bonds; log S—Logarithm of intrinsic aqueous solubility in mM; log S7.4—Logarithm of solubility in phosphate buffered solution at pH 7.4.

In the Drug_data and Aquatic_tox data seta the following additional property was included: log BB—Blood brain barrier penetration as the logarithm of brain:blood concentration ratio These properties in the Oral_F Drug data and Aquatic_tox data sets were calculated using QSAR models in the StarDrop™ software developed and sold by Optibrium Ltd.

Example 1

Objectives

In this example, an objective of identifying compounds with good oral bioavailability in humans has been employed (a typical drug discovery objective). Oral bioavailability is a measure of the amount of a dose that reaches the systemic circulation following oral administration of a compound. For this purpose, good oral bioavailability was defined as greater than or equal to 30%.

Method

The Oral_F data set was used as the training data set to determine criteria to find compounds with a high probability of having good oral bioavailability in humans using the properties included in the Oral_F data set. An embodiment of the process shown in FIG. 2A was applied wherein the bump hunting embodiment was applied to determine the selection criteria and the probability density estimation embodiment was applied to determine the importance values.

For the purposes of validation, the Oral_F data set was divided into separate training (75%) and test (25%) data sets. The selection criteria for the properties listed above were determined from the training data set and the performance of the selection criteria in accurately distinguishing test compounds with good oral bioavailability from those with poor oral bioavailability was validated using the independent test data set. This was repeated 100 times with different training and test data set splits to rigorously evaluate the performance of the method.

Finally, an embodiment of the process described in FIG. 2A was applied using the full Oral_F data set as the training data set to determine sets of criteria using a bump hunting embodiment and their importance values using a probability density estimation embodiment.

Results

Figure 8:
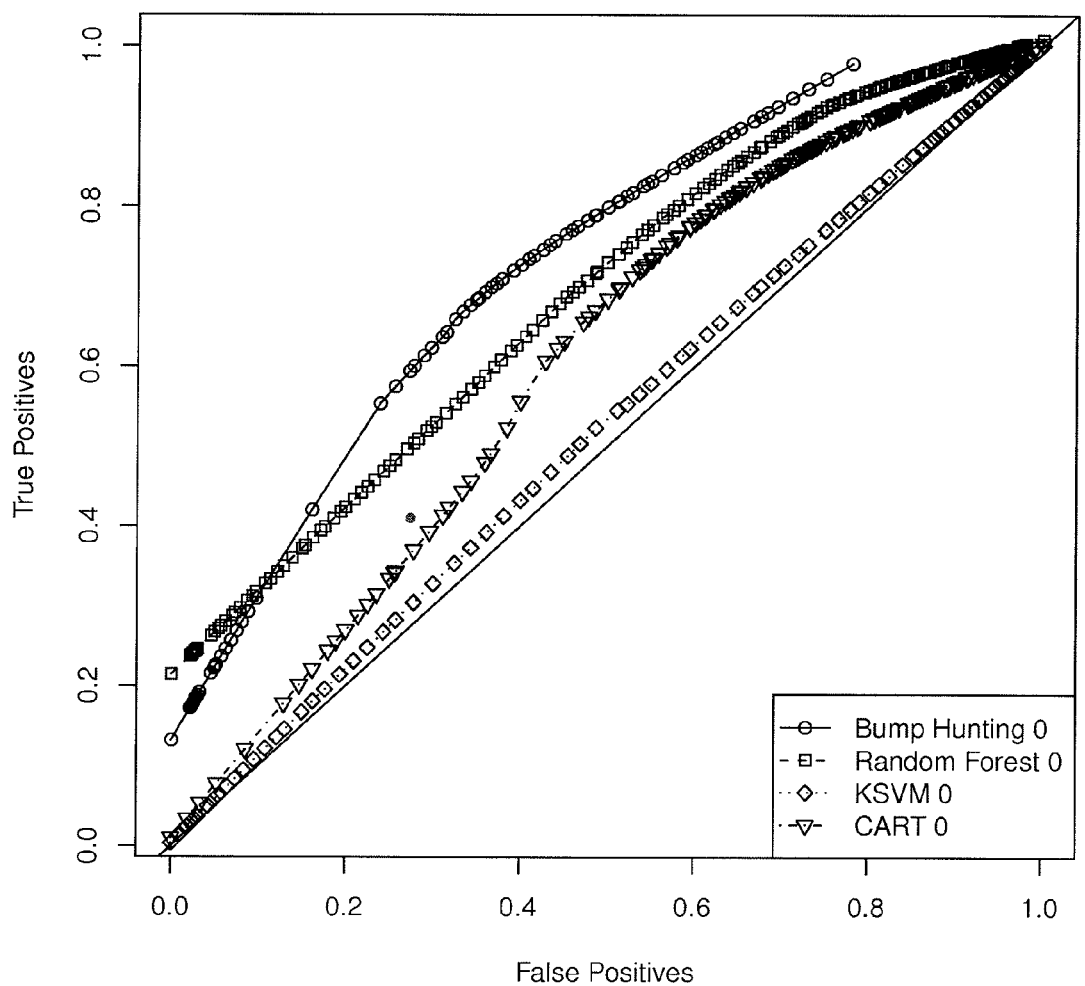
FIG. 8 illustrates Receiver Operator Characteristic (ROC) curves for oral bioavailability.

FIG. 8 is a plot of Receiver Operator Characteristic (ROC) curves comparing the performance of a bump hunting embodiment with other machine learning algorithms, Random Forest, Kernel Support Vector Machines (KSVM) and Classification and Regression Trees (CART) for identification of training compounds that meet the objective, in this case good oral bioavailability. From this, it can be seen that the performance of the bump hunting embodiment exceeds the other techniques in accurately distinguishing compounds that meet the objective of good oral bioavailability from those that do not.

The sets of selection criteria identified were as follows:

|  |  | logP | HBA | HBD | logS7.4 | Flex | TPSA | MW | Rotatable Bonds | logD | logS |
|---|---|---|---|---|---|---|---|---|---|---|---|
| Criteria set 1 | Upper bound | −4.78 | 3.00 | 0.12 | 2.10 | 0.00 | 36.17 | 0.00 | 1.00 | 0.00 | −2.97 |
|  | Lower bound | 8.71 | 9.17 | 3.00 | 4.81 | 0.85 | 119.10 | 401.61 | 20.9 | 3.23 | 5.14 |
| Criteria set 2 | Upper bound | 0.14 | 2.00 | 0.00 | 0.82 | 0.14 | 28.12 | 0.00 | 3.00 | 0.00 | 1.88 |
|  | Lower bound | 4.44 | 35.1 | 2.00 | 3.06 | 0.85 | 112.70 | 508.92 | 10.00 | 2.72 | 5.01 |
| Criteria set 3 | Upper bound | −4.78 | 0.00 | 0.00 | 1.50 | 0.00 | 38.36 | 132.52 | 0.00 | 0.00 | 1.15 |
|  | Lower bound | 3.55 | 9.00 | 19.80 | 8.80 | 0.85 | 554.95 | 406.03 | 6.0 | 3.98 | 8.80 |
| Criteria set 4 | Upper bound | 2.58 | 0.00 | 0.00 | −2.97 | 0.00 | 3.24 | 227.85 | 0.00 | 0.00 | −2.97 |
|  | Lower bound | 8.71 | 35.1 | 1.93 | 3.07 | 0.31 | 121.73 | 341.33 | 8.0 | 3.32 | 8.80 |
| Criteria set 5 | Upper bound | −4.78 | 0.00 | 0.00 | −2.97 | 0.08 | −50.45 | 0.00 | 0.00 | 0.00 | −2.97 |
|  | Lower bound | 8.71 | 35.10 | 19.80 | 4.43 | 0.85 | 554.95 | 752.90 | 11.26 | 8.76 | 8.80 |
| Criteria set 6 | Upper bound | −0.51 | 0.00 | 0.00 | 1.39 | 0.00 | 19.69 | 0.00 | 0.00 | 0.00 | 0.85 |
|  | Lower bound | 8.71 | 35.10 | 19.80 | 8.80 | 0.85 | 554.95 | 826.21 | 16.0 | 8.76 | 8.80 |
| Criteria set 7 | Upper bound | −1.49 | 0.00 | 0.00 | −2.97 | 0.00 | 18.90 | 0.00 | 0.00 | 0.00 | −2.97 |
|  | Lower bound | 8.71 | 35.10 | 19.80 | 8.80 | 0.85 | 554.95 | 1586.00 | 17.47 | 8.76 | 8.80 |
| Criteria set 8 | Upper bound | −4.78 | 0.00 | 0.00 | −2.97 | 0.00 | −50.45 | 0.00 | 0.00 | 0.00 | −2.97 |
|  | Lower bound | 8.71 | 35.10 | 19.80 | 8.80 | 0.85 | 554.95 | 1586.00 | 20.9 | 8.761 | 8.80 |

Figure 9:
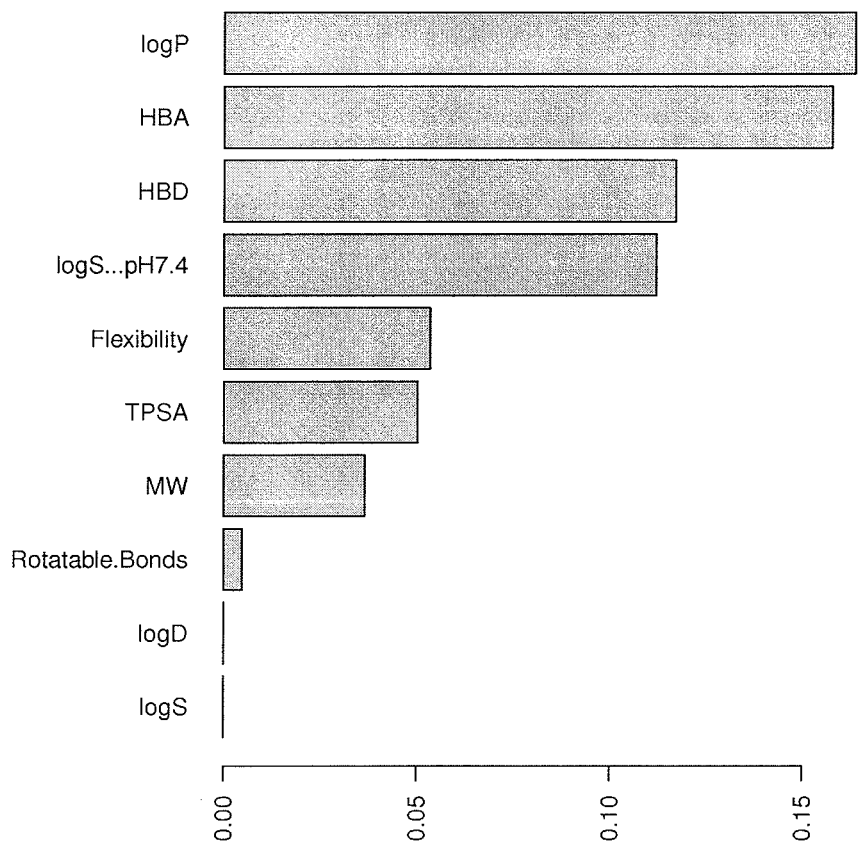
FIG. 9 is a bar chart showing importance values.

FIG. 9 is a bar chart showing the importance values of each property in a set of selection criteria for an objective of oral bioavailability.

Example 2

Objective

In this example, the objective of identifying compounds with good oral bioavailability in humans has been employed (a typical drug discovery objective). Oral bioavailability is a measure of the amount of a dose that reaches the systemic circulation following oral administration of a compound. For this purpose, good oral bioavailability has been defined as greater than or equal to 30%.

Method

The Oral_F data set was used as the training data set to determine criteria to find compounds with a high probability of having good oral bioavailability in humans using the properties included in the data set. An embodiment of the process shown in FIG. 2B was applied, wherein the bump hunting embodiment was applied to determine the selection criteria and a probability density estimation embodiment was applied to determine the importance values. The selection criteria determined from the Oral_F training data set were then applied to a test data set, comprising the compounds in the Drug_data data set, to indicate those compounds most likely to exhibit good oral bioavailability. The probability density estimation embodiment was applied to calculate scores for each of the test compounds in Drug_data.

As the routes of administration are known for these compounds, the ability of the selection criteria can be tested for their ability to discriminate between orally administered compounds (oral) from those that are not administered orally (non-oral) in the test data set. This can be used as a surrogate objective for oral bioavailability, but it should be noted that an approved oral route of administration does not necessarily imply oral bioavailability of greater than or equal to 30%. Nor does the fact that a compound is only used via non-oral administration necessarily mean that it is not orally bioavailable. Therefore, even if the selection criteria were perfect at distinguishing compounds with good oral bioavailability from those with poor oral bioavailability, a perfect distinction between oral and non-oral compounds in the Drug_data data set would not be expected. However, some distinction in the distribution of scores for oral and non-oral compound would be expected.

Results

Figure 10:
FIG. 10 is an example output of scores for test compounds in a Drug_data data set.

FIG. 10 is an example output of scores for test compounds in the Drug_data set data set calculated using the selection criteria and importance values determined from the training data set, Oral_F, to select compounds with high oral bioavailability.

Figure 11:
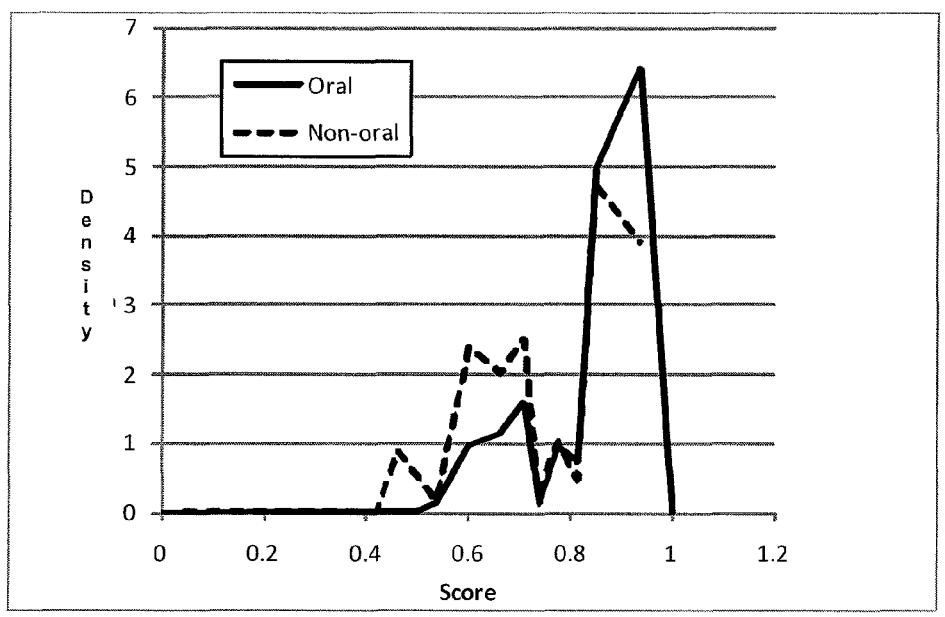
FIG. 11 illustrates probability distributions for the scores of the test compounds in the Drug_data data set.

FIG. 11 is a plot of probability distributions for the scores of the test compounds in the Drug_data set data set calculated using the selection criteria and importance values determined from the training data set, Oral_F, to select compounds with high oral bioavailability. For comparison, the probability distributions for orally administered drug (Oral) and drugs that are not administered orally (Non-oral) are shown separately. From this it can be seen that test compounds that are administered orally have a high probability of achieving a high score than those that are not administered orally. Furthermore, only a small proportion of the orally administered test compounds have a low calculated score.

For example, 48% of test compounds that are not orally dosed receive a score less than or equal to 0.8, while only 26% of test compounds that are orally dosed receive scores less than or equal to 0.8. Therefore, if only test compounds with scores above 0.8 are selected, roughly half of the non-oral compounds would be rejected, with the loss of only about one quarter of the oral. Given the 'noisy' nature of this data, this is a very positive result.

Example 3

Objective

In this example, the objective of identifying compounds that are suitable both for oral administration and also for a therapeutic target in the CNS has been employed. This illustrates the ability of the method to identify selection criteria for complex combined objectives that are typical in drug discovery.

Method

The Drug_data data set was used as a training set to identify selection criteria for compounds with a high probability of being suitable both for oral administration and for a target in the CNS. An embodiment of the process in FIG. 2A was applied wherein the bump hunting embodiment was applied to determine the selection criteria and the probability density estimation embodiment was applied to determine the importance values.

The Drug_data data set was divided into separate training (75%) and test (25%) data sets for the purposes of validation. The selection criteria for the properties listed above were determined from the training data set and the performance of the selection criteria in accurately identifying compounds that meet the objective was validated using the independent test data set. This was repeated 100 times with different training and test data set splits to rigorously evaluate the performance of the method.

Finally, having validated the method, an embodiment of the process described in FIG. 2A was applied using the full Drug_data data set as the training data set, wherein the bump hunting embodiment was applied to determine sets of selection criteria and the probability density estimation embodiment was applied to determine their importance values.

Results

Figure 12:
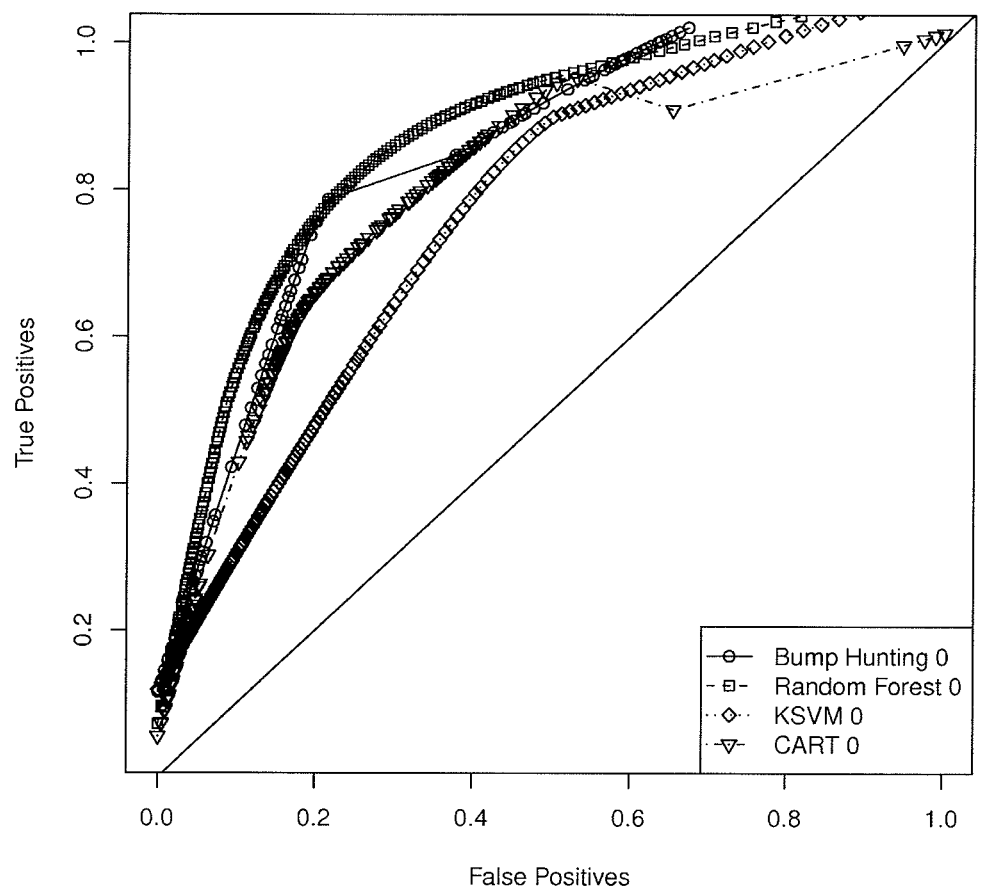
FIG. 12 illustrates Receiver Operator Characteristic (ROC) curves for CNS and oral bioavailability.

FIG. 12 is a plot of Receiver Operator Characteristic (ROC) curves comparing the performance of a bump hunting embodiment with other machine learning algorithms, Random Forest, Kernel Support Vector Machines (KSVM) and Classification and Regression Trees (CART) for identification of training compounds that meet the objective, in this case a combination of oral bioavailability and CNS penetration. From this, it can be seen that bump hunting embodiment exceeds the performance of these techniques, other than Random Forest, in accurately identifying compounds that meet the objective.

The sets of selection criteria identified were as follows:

Example 4

Objective

In this example, the objective of identifying compounds that have low aquatic toxicity, as measured by the 50% inhibitory growth concentration of *Tetrahymena Pyriformis* ($IGC_{50}$) has been employed. In this case, compounds with low aquatic toxicity were defined as those with $IGC_{50}$ greater than 1 mg/l. This is an example of an application in the agrochemical or industrial chemical industries.

Method

The Aquatic_tox data set was used to determine selection criteria to find compounds with a high probability of having low aquatic toxicity using the properties included in the Aquatic_tox data set. An embodiment of the process in FIG. 2A was applied wherein the bump hunting embodiment was applied to determine the selection criteria and the probability density estimation embodiment was applied to determine the importance values.

The Aquatic_tox data set was divided into separate training (75%) and test (25%) data sets for the purposes of validation. The selection criteria for the properties listed above were determined from the training set and the performance of the criteria in accurately distinguishing test compounds with low aquatic toxicity from those with high aquatic toxicity was validated using the test data set. This was repeated 100 times with different training and test data set splits to rigorously evaluate the performance of the method.

Finally, having validated the method, an embodiment of the process described in FIG. 2A was applied to the full Aquatic_tox data set, wherein the bump hunting embodiment was applied to determine sets of selection criteria and the probability density estimation embodiment was applied to determine their importance values.

|  |  | logP | HBA | HBD | LogS7.4 | Flex | TPSA | MW | Rotatable Bonds | logD | logS | logBB |
|---|---|---|---|---|---|---|---|---|---|---|---|---|
| Criteria Set 1 | Lower bound | 1.07 | 1.00 | 0.00 | −2.85 | 0.00 | 0.00 | 180.34 | 0.00 | 0.77 | 1.57 | −0.17 |
|  | Upper bound | 8.54 | 5.00 | 2.00 | 9.65 | 0.26 | 76.80 | 301.20 | 5.00 | 2.87 | 4.43 | 2.42 |
| Criteria Set 2 | Lower bound | −0.14 | 0.00 | 0.00 | 2.18 | 0.00 | 24.63 | 0.00 | 0.00 | −0.29 | −2.73 | −1.77 |
|  | Upper bound | 8.54 | 5.00 | 2.00 | 9.65 | 0.24 | 62.28 | 493.86 | 10.00 | 3.07 | 5.19 | 2.42 |
| Criteria Set 3 | Lower bound | 0.63 | 1.00 | 0.00 | 1.02 | 0.03 | 12.47 | 0.00 | 0.00 | 0.35 | −2.73 | −8.49 |
|  | Upper bound | 8.54 | 5.00 | 2.00 | 9.65 | 0.38 | 72.68 | 335.91 | 6.14 | 2.43 | 8.30 | 2.42 |
| Criteria Set 4 | Lower bound | 1.84 | 0.00 | 0.00 | −2.85 | 0.12 | 0.00 | 305.46 | 0.00 | 0.21 | 1.21 | −0.52 |
|  | Upper bound | 8.54 | 93.50 | 2.00 | 2.91 | 0.34 | 71.11 | 484.27 | 10.00 | 4.69 | 3.43 | 2.42 |
| Criteria Set 5 | Lower bound | 0.16 | 0.00 | 0.00 | −2.85 | 0.04 | 0.00 | 0.00 | 0.00 | −0.55 | −2.73 | −1.95 |
|  | Upper bound | 8.54 | 6.00 | 3.00 | 4.35 | 1.00 | 109.22 | 312.19 | 9.38 | 3.31 | 5.27 | 2.42 |
| Criteria Set 6 | Lower bound | −0.02 | 3.00 | 0.00 | 1.28 | 0.00 | 40.47 | 0.00 | 0.00 | −1.56 | −2.73 | −2.03 |
|  | Upper bound | 4.50 | 93.50 | 3.00 | 3.48 | 1.00 | 120.25 | 3366.20 | 7.48 | 10.60 | 4.45 | 0.15 |
| Criteria Set 7 | Lower bound | −5.36 | 2.00 | 0.00 | −2.85 | 0.00 | 0.00 | 0.00 | 0.00 | −2.52 | 0.20 | −0.62 |
|  | Upper bound | 5.70 | 7.00 | 2.37 | 4.15 | 1.00 | 87.77 | 466.31 | 11.00 | 4.88 | 8.30 | 2.42 |
| Criteria Set 8 | Lower bound | 0.01 | 0.00 | 0.00 | 0.27 | 0.00 | 28.84 | 0.00 | 0.00 | −0.22 | −2.73 | −1.08 |
|  | Upper bound | 8.54 | 93.50 | 57.20 | 9.65 | 0.34 | 1563.10 | 416.71 | 149.60 | 10.60 | 8.30 | 2.42 |

Figure 13:
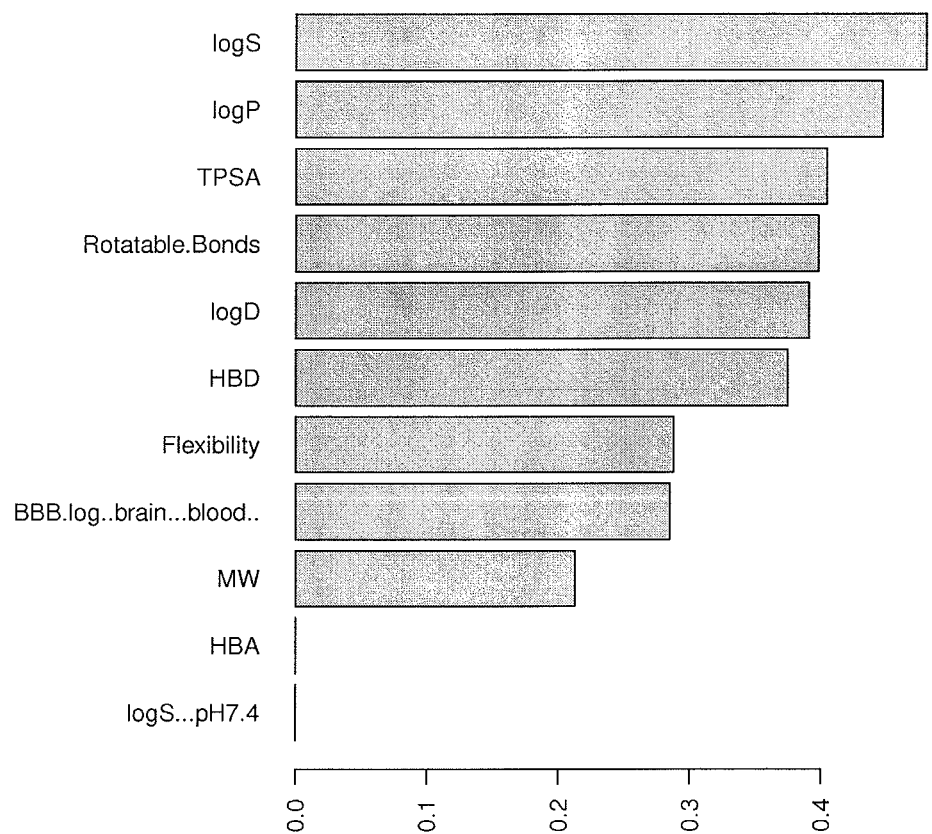
FIG. 13 is a bar chart showing the importance values for CNS and oral bioavailability.

FIG. 13 is a bar chart showing the importance values of each property in a set of selection criteria for an objective of a combination of oral bioavailability and CNS penetration.

This illustrates that the selection criteria provide valuable guidance as to appropriate selection criteria, even for imprecise data such as that often available in drug discovery.

Results

Figure 14:
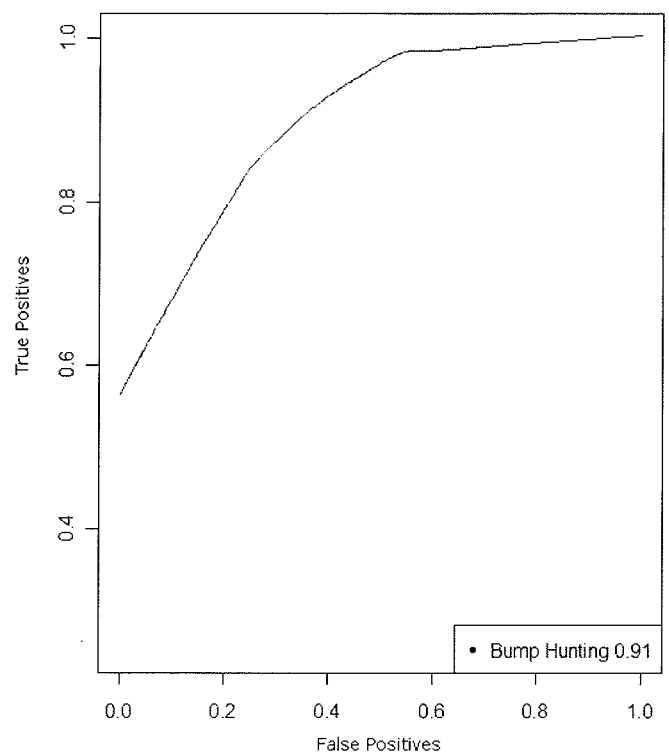
FIG. 14 is a Receiver Operator Characteristic (ROC) curve for low aquatic toxicity.

FIG. 14 is a plot of Receiver Operator Characteristic (ROC) curve showing the performance of the bump hunting embodiment in identifying test compounds that meet the objective of low aquatic toxicity. From this, it can be seen that the selection criteria can accurately distinguish between compounds with high and low aquatic toxicity.

The sets of criteria identified were as follows:

|  | logS | logS7.4 | logP | logD | logBB | MW | HBD | HBA | TPSA | Flex | Rotatable Bonds |
|---|---|---|---|---|---|---|---|---|---|---|---|
| Criteria Set 1 | 4.33 8.45 | −0.18 6.57 | −2.66 1.76 | −4.60 1.43 | −1.30 1.03 | 0.00 118.03 | 0.00 4.40 | 0.00 7.70 | 17.07 129.47 | 0.00 0.92 | 0.00 5.00 |
| Criteria Set 2 | 4.27 8.45 | 3.32 8.45 | −0.34 1.98 | −4.60 3.42 | −1.30 1.03 | 0.00 156.90 | 0.00 4.40 | 0.00 7.70 | 17.07 54.30 | 0.00 0.92 | 0.00 5.00 |
| Criteria Set 3 | 3.88 8.45 | −0.18 4.98 | −2.66 1.95 | −4.60 1.67 | −1.30 0.32 | 120.14 462.87 | 0.00 2.00 | 0.00 7.70 | 0.00 74.60 | 0.00 0.67 | 0.00 12.10 |
| Criteria Set 4 | 3.89 8.45 | −0.18 8.45 | −2.66 5.72 | −4.60 2.88 | −1.30 1.03 | 0.00 175.34 | 0.00 4.40 | 0.00 7.70 | 17.07 129.47 | 0.00 0.67 | 0.00 12.10 |
| Criteria Set 5 | 3.26 8.45 | −0.18 8.45 | −2.66 5.72 | −4.60 3.05 | −1.30 0.59 | 0.00 219.17 | 0.00 4.40 | 0.00 7.70 | 0.00 91.64 | 0.00 0.72 | 0.00 12.10 |

Figure 15:
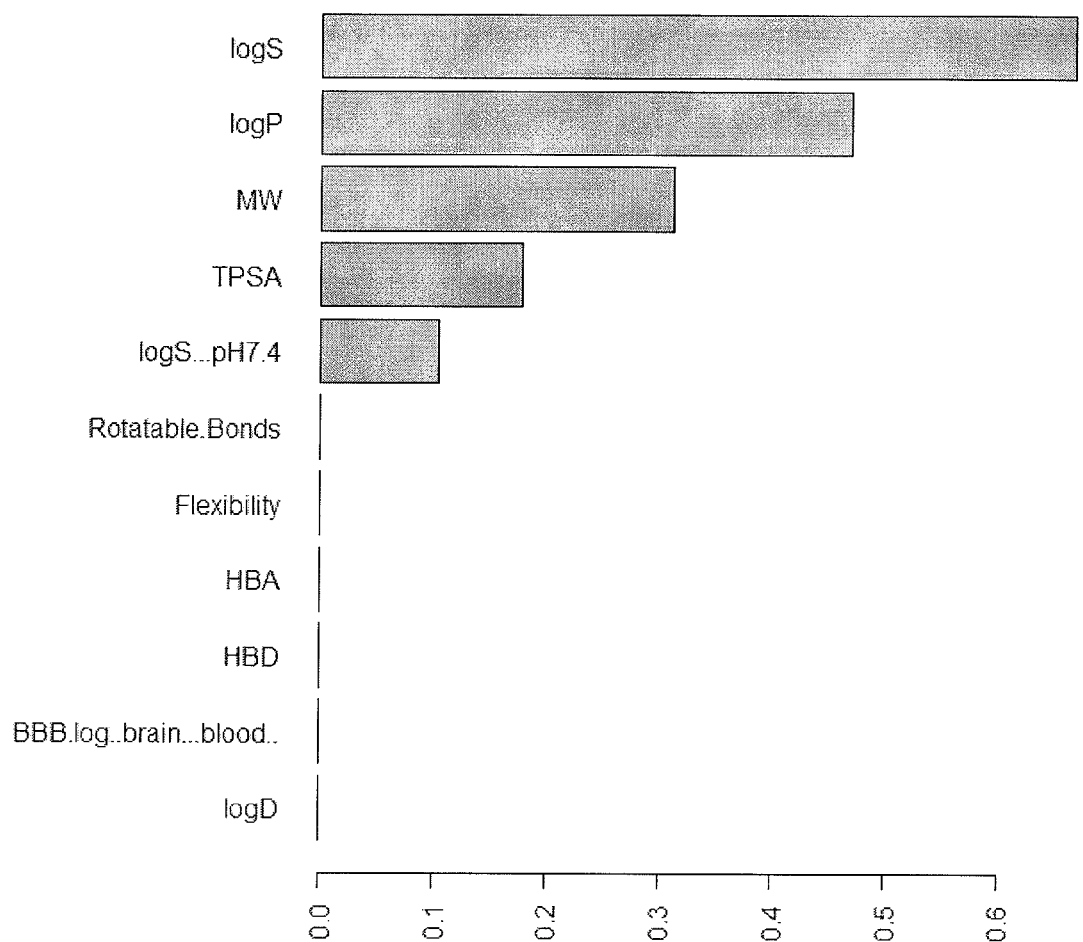
FIG. 15 is a bar chart showing the importance values for low aquatic toxicity.

FIG. 15 is a bar chart showing the importance values of each property in a set of selection criteria for an objective of low aquatic toxicity.

This disclosure is to be broadly construed. It is intended that the invention disclosed herein in its many embodiments be protected on all types of computer technology, for all types of computer processing, on all types of computer readable media and for all types of transmissions. Each embodiment disclosed herein is a computer product, computer program product, computer software product, computer usable medium product and computer system product. Each embodiment disclosed herein can comprise a computer system and this disclosure supports computer system claims to each embodiment as a computer system. Each embodiment disclosed herein can comprise a computer program product or a computer software product and this disclosure supports claims to each embodiment as a computer program product or computer software product. The embodiments herein are to computer methods, computer systems, computer networks, computer program products, computer software products, computer readable medium articles and are able to be transmitted by a variety of means including by network, internet, wired and wireless communications, as well as from one computer readable medium to another.

The embodiments disclosed herein can be provided to a user installed on a computer system, on a computer readable medium, by means of transmission over a network, or by other means. The embodiments can be provide to a user in-part or in whole, as one integrated whole or in parts or pieces or modules. It intended that this disclosure be broad and broadly construed to support claims across all computer technologies, computer systems, computer networks and in any form which the embodiments disclosed herein can be provided to a computer, computer system, computer network or user.

Using the description provided herein, the embodiments can be implemented as a machine, process, or article of manufacture by using standard programming and/or engineering techniques to produce programming software, firmware, hardware or any combination thereof.

Any resulting program(s), having computer-readable program code, can be embodied on one or more computer-usable media such as resident memory devices, smart cards or other removable memory devices, or transmitting devices, thereby making a computer program product or article of manufacture according to the embodiments. The method can be provided as a software product by any machine readable medium and not limited to CD ROM, DVD ROM, internet, hard disk, USB drive, Flash RAM.

The capabilities of exemplary embodiments of present invention described above can be implemented in software, firmware, hardware, or some combination thereof, and can be realized in a centralized fashion in one computer system, or in a distributed fashion where different elements are spread across several interconnected computer systems. Any kind of computer system—or other apparatus adapted for carrying out the methods and/or functions described herein—is suitable. A typical combination of hardware and software could be a general purpose computer system with a computer program that, when being loaded and executed, controls the computer system such that it carries out the methods described herein. Exemplary embodiments of the present invention can also be embedded in a computer program product, which comprises features enabling the implementation of the methods described herein, and which—when loaded in a computer system—is able to carry out these methods.

Computer program means or computer program in the present context include any expression, in any language, code or notation, of a set of instructions intended to cause a system having an information processing capability to perform a particular function either directly or after conversion to another language, code or notation, and/or reproduction in a different material form.

Therefore, one or more aspects of exemplary embodiments of the present invention can be included in an article of manufacture (for example, one or more computer program products) having, for instance, computer usable media. The media has embodied therein, for instance, computer readable program code means for providing and facilitating the capabilities of the present invention. The article of manufacture can be included as a part of a computer system or sold separately. Furthermore, at least one program storage device readable by a machine, tangibly embodying at least one program of instructions executable by the machine to perform the capabilities of the exemplary embodiments of the present invention described above can be provided.

The above-described program or modules implementing exemplary embodiments of the present invention can work on a computer exemplified by FIG. 1 and the like. The program or modules implementing exemplary embodiments can be stored in an external storage medium. In addition to a disk, an optical recording medium such as a DVD and a PD, a magneto-optical recording medium such as a MD, a tape medium, a semiconductor memory such as an IC card, and the like can be used as the storage medium. Moreover, the program can be provided to computer 100 through the network by using, as the recording medium, a storage device such as a hard disk or a RAM, which is provided in a server system connected to a dedicated communication network or the Internet.

While exemplary embodiments of the present invention have been described, it will be understood that those skilled in the art, both now and in the future, can make various modifications without departing from the spirit and the scope of the present invention as set forth in the following claims. These following claims should be construed to maintain the proper protection for the present invention.

We claim:

1. A method executed on a computer for analysis of property data, comprising the steps of:
   providing a computer having a memory;
   providing to said memory a training data from a training data set comprising at least one training compound with at least one property value for each said training compound;
   providing to said memory a label data identifying each said training compound as achieving an objective or not achieving said objective;
   a. said computer running a program executable code on said training data set defining a box in the space of properties containing all of the training compounds in the training data set;
   b. said computer running a program executable code performing one or more peeling steps, whereby each peeling step compresses said box removing a proportion of the training compounds $\gamma$ from said box, wherein $\gamma$ can take a value greater than 0 and less than 1;
   c. said computer running a program executable code performing zero or more pasting steps, whereby each pasting step expands said box adding back a proportion of the training compounds $\beta$ into said box, wherein $\beta$ can take a value greater than 0 and less than 1;
   d. said computer running a program executable code determining the selection criteria on at least one property corresponding to the boundaries of the resulting box;
   e. said computer running a program executable code removing the training compounds in the box from the training data set;
   said computer running a program executable code repeating steps a through e until a predefined stopping condition for construction of boxes has been met; and
   said computer running a program executable code determining an importance value for each selection criterion.

2. The method of claim 1, wherein the step of determining an importance value for each selection criteria comprises the step of:
   said computer running a program executable code calculating the importance value for each selection criterion by determining the ratio between the probability that a training compound meeting a selection criterion achieves the objective and the probability that a training compound that does not meet the selection criterion achieves said objective.

3. The method of claim 1, in which said objective is a drug discovery objective.

4. The method of claim 3, wherein the step of determining an importance value for each selection criteria comprises the step of:
   said computer running a program executable code calculating the importance value for each selection criterion by determining the ratio between the probability that a training compound meeting a selection criterion achieves said drug discovery objective and the probability that a training compound that does not meet the selection criterion achieves said drug discovery objective.

5. A method executed on a computer for selection of compounds, comprising the steps of:
   providing a computer having a memory;
   providing to said memory a training data from a training data set comprising at least one training compound with at least one property value for each said training compound;
   providing to said memory a label data identifying each said training compound as achieving an objective or not achieving said objective;
   a. said computer running a program executable code on said training data set defining a box in the space of properties containing all of the training compounds in the training data set;
   b. said computer running a program executable code performing one or more peeling steps, whereby each peeling step compresses said box removing a proportion of the training compounds $\gamma$ from said box, wherein $\gamma$ can take a value greater than 0 and less than 1;
   c. said computer running a program executable code performing zero or more pasting steps, whereby each pasting step expands said box adding back a proportion of the training compounds $\beta$ into said box, wherein $\beta$ can take a value greater than 0 and less than 1;
   d. said computer running a program executable code determining the selection criteria on at least one property corresponding to the boundaries of the resulting box;
   e. said computer running a program executable code removing the training compounds in the box from the training data set;
   said computer running a program executable code repeating steps a through e until a predefined stopping condition for construction of boxes has been met;
   said computer running a program executable code determining an importance value for each selection criterion;
   providing a test data from a test data set comprising at least one test compound and at least one property value for each test compound, wherein at least one test compound has a property which can be compared to a property of a training compound having a value present in the training data set;
   said computer running a program executable code applying one or more of the selection criteria to identify test compounds that meet the selection criteria.

6. The method of claim 5, in which said objective is a drug discovery objective.

7. The method of claim 5, wherein the step of determining an importance value for each selection criterion further comprising the steps of:
   said computer outputting the selection criteria and corresponding importance values reflecting the importance of each criterion,
   receiving into said memory a user input to modify the selection criteria and/or importance value of one or more selection criterion.

8. The method of claim 5 further comprising the step of:
   said computer outputting at least one value for each test compound in the test set, indicating those test compounds most likely to meet the objective.

9. The method of claim 5, wherein the step of determining an importance value for each selection criteria comprises the step of:
   said computer running a program executable code calculating the importance value for each selection criterion by determining the ratio between the probability that a training compound meeting a selection criterion achieves the objective and the probability that a training compound that does not meet the selection criterion achieves the objective.

10. The method of claim 6, wherein the step of determining an importance value for each selection criterion further comprising the steps of:
said computer outputting the selection criteria and corresponding importance values reflecting the importance of each criterion,
receiving into said memory a user input to modify the selection criteria and/or importance value of one or more selection criterion.

11. The method of claim 6 further comprising the step of:
said computer outputting at least one value for each test compound in the test set,
indicating those test compounds most likely to meet the drug discovery objective.

12. The method of claim 6, wherein the step of determining an importance value for each selection criteria comprises the step of:
said computer running a program executable code calculating the importance value for each selection criterion by determining the ratio between the probability that a training compound meeting a selection criterion achieves the drug discovery objective and the probability that a training compound that does not meet the selection criterion achieves the drug discovery objective.

13. The method of claim 10, further comprising the step of:
said computer outputting at least one value for each test compound in the test set,
indicating those test compounds most likely to meet the drug discovery objective.

14. The method of claim 10, wherein the step of determining an importance value for each selection criteria comprises the step of:
said computer running a program executable code calculating the importance value for each selection criterion by determining the ratio between the probability that a training compound meeting a selection criterion achieves the drug discovery objective and the probability that a training compound that does not meet the selection criterion achieves the drug discovery objective.

15. The method of claim 11, wherein the step of determining an importance value for each selection criteria comprises the step of:
said computer running a program executable code calculating the importance value for each selection criterion by determining the ratio between the probability that a training compound meeting a selection criterion achieves the drug discovery objective and the probability that a training compound that does not meet the selection criterion achieves the drug discovery objective.

16. The method of claim 7 further comprising the step of:
said computer outputting at least one value for each test compound in the test set,
indicating those test compounds most likely to meet the objective.

17. The method of claim 7, wherein the step of determining an importance value for each selection criteria comprises the step of:
said computer running a program executable code calculating the importance value for each selection criterion by determining the ratio between the probability that a training compound meeting a selection criterion achieves the objective and the probability that a training compound that does not meet the selection criterion achieves the objective.

18. The method of claim 16, wherein the step of determining an importance value for each selection criteria comprises the step of:
said computer running a program executable code calculating the importance value for each selection criterion by determining the ratio between the probability that a training compound meeting a selection criterion achieves the objective and the probability that a training compound that does not meet the selection criterion achieves the objective.

19. The method of claim 8, wherein the step of determining an importance value for each selection criteria comprises the step of:
said computer running a program executable code calculating the importance value for each selection criterion by determining the ratio between the probability that a training compound meeting a selection criterion achieves the objective and the probability that a training compound that does not meet the selection criterion achieves the objective.

* * * * *